United States Patent
Hanada et al.

(10) Patent No.: US 10,379,183 B2
(45) Date of Patent: Aug. 13, 2019

(54) MAGNETIC MOMENT ARRANGEMENT CALCULATION METHOD FOR MAGNETIC FIELD ADJUSTMENT, MAGNETIC FIELD ADJUSTMENT DEVICE AND PROGRAM

(71) Applicant: HITACHI, LTD., Tokyo (JP)

(72) Inventors: Hikaru Hanada, Tokyo (JP); Kenji Sakakibara, Tokyo (JP); Mitsushi Abe, Tokyo (JP); Takuya Fujikawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 278 days.

(21) Appl. No.: 15/541,838

(22) PCT Filed: Jan. 27, 2016

(86) PCT No.: PCT/JP2016/052258
§ 371 (c)(1),
(2) Date: Jul. 6, 2017

(87) PCT Pub. No.: WO2016/132831
PCT Pub. Date: Aug. 25, 2016

(65) Prior Publication Data
US 2018/0003784 A1 Jan. 4, 2018

(30) Foreign Application Priority Data
Feb. 20, 2015 (JP) .................. 2015-032325

(51) Int. Cl.
*G01R 33/3875* (2006.01)
*A61B 5/055* (2006.01)
*G01R 33/3873* (2006.01)

(52) U.S. Cl.
CPC .......... *G01R 33/3875* (2013.01); *A61B 5/055* (2013.01); *G01R 33/3873* (2013.01)

(58) Field of Classification Search
CPC .. G01R 33/3875; G01R 33/3873; A61B 5/055
(Continued)

(56) References Cited

U.S. PATENT DOCUMENTS

| | | | |
|---|---|---|---|
| 2011/0089943 A1 | 4/2011 | Abe et al. | |
| 2012/0268119 A1* | 10/2012 | Abe | G01R 33/3873 324/307 |
| 2014/0009152 A1 | 1/2014 | Sakakibara | |

FOREIGN PATENT DOCUMENTS

| | | |
|---|---|---|
| JP | 4902787 B2 | 3/2012 |
| WO | WO2012/132911 A1 | 10/2012 |
| WO | WO2015/005109 A1 | 1/2015 |

OTHER PUBLICATIONS

International Search Report dated Mar. 8, 2016 in connection with PCT/JP2016/052258.

(Continued)

*Primary Examiner* — Melissa J Koval
*Assistant Examiner* — Rahul Maini
(74) *Attorney, Agent, or Firm* — Cooper & Dunham LLP

(57) ABSTRACT

A magnetic moment arrangement calculation method for magnetic field adjustment by combining correction of a component of a low-order mode with correction of a component of a high-order mode among the eigenmodes so as to calculate arrangement of the magnetic moment for approximately correcting the error magnetic field distribution, in which the low-order mode is an eigenmode group from the first of eigenmode numbers assigned to respective eigenmodes in the magnitude order of singular values to an eigenmode number specified by a first threshold value, in which the high-order mode is an eigenmode group with an eigenmode number more than the first threshold value, and in which a correction amount of the component of the (Continued)

high-order mode is smaller than a correction amount of the component of the low-order mode.

14 Claims, 16 Drawing Sheets

(58) Field of Classification Search
USPC .......................................................... 324/314
See application file for complete search history.

(56) References Cited

OTHER PUBLICATIONS

Mitsushi Abe et al. "A technique to determine co-axial coil placements of a magnet for accurate magnetic field" The 24$^{th}$ Symposium on Electromagnets and Dynamics May 16, 2012, 79-82.

Mitsushi Abe "Magnetic Field Distribution Adjustment Method Using Regularization Calculation by Censored Singular Value Decomposition" 42nd Magnetic Resonance Medical Society of Japan, Sep. 19, 2014.

Mitsushi Abe et al., "Consideration on Current and Coil Block Placements With Good Homogeneity for MRI Magnets Using Truncated SVD," in *IEEE Transactions on Magnetics*, vol. 49, No. 6, pp. 2873-2880, Jun. 2013.

Mitsushi Abe "Magnetic field correction through iron piece placements calculated by truncated singular value decomposition" The 27$^{th}$ Symposium on Electromagnets and Dynamics May 14, 2015, 465-468.

Mitsushi Abe et al., "Coil Block Designs With Good Homogeneity for MRI Magnets Based on SVD Eigenmode Strengths," *IEEE Transactions on Magnetics*, vol. 51, No. 10, pp. 1-13, Oct. 2015.

* cited by examiner

MAGNETIC MOMENT ARRANGEMENT CALCULATION METHOD FOR MAGNETIC FIELD ADJUSTMENT, MAGNETIC FIELD ADJUSTMENT DEVICE AND PROGRAM

TECHNICAL FIELD

The present invention relates to a magnetic resonance imaging (hereinafter, referred to as an MRI) apparatus which measures a nuclear magnetic resonance signal (hereinafter, referred to as an NMR signal) from hydrogen, phosphor, or the like of an object, and generates a nuclear density distribution or a relaxation time distribution as an image, and particularly to a technique of uniformizing a static magnetic field in a measurement region.

BACKGROUND ART

An MRI apparatus is an apparatus which measures an NMR signal generated by atomic nucleus spins forming an object, especially, tissues of a human body, and generates morphologies or functions of the head, the abdomen, and the limbs thereof as two-dimensional or three-dimensional images.

A spatially uniform static magnetic field is necessary in a region in which an NMR signal is measured. This is because the homogeneity of a static magnetic field influences image quality (distortion or luminance unevenness of an image, an SNR, and the like). In order to uniformize a static magnetic field in a measurement region, magnetic field adjustment (shimming) is performed so that a substance (hereinafter, simply referred to as magnetic moment) having a magnetic moment of a predetermined magnitude, such as an iron piece is disposed at a predetermined position. The shimming includes, for example, a method of determining arrangement of a magnetic moment by using singular value decomposition (refer to PTL 1).

CITATION LIST

Patent Literature

PTL 1: Japanese Patent No. 4902787

SUMMARY OF INVENTION

Technical Problem

In the method disclosed in PTL 1, arrangement of a magnetic moment which generates a magnetic field distribution for canceling an error magnetic field from a nonuniform magnetic field distribution (error magnetic field) of a static magnetic field is obtained. This computation corresponds to an inverse problem for obtaining arrangement of a magnetic moment in a magnetic field, and truncated singular value decomposition is used to solve the problem. In the truncated singular value decomposition, in order to reduce an error magnetic field within a realistic range, among respective eigenmodes obtained through the singular value decomposition, correction is preferentially performed from an eigenmode having the great influence, and the maximum correction effect is achieved within a restricted magnetic moment amount.

However, if an eigenmode to be corrected is increased by one, an iron amount required for correction changes stepwise. Thus, in a case where correction is performed in a restricted magnetic moment amount, only a predetermined number of eigenmodes can be corrected, and thus a magnetic moment amount may remain. As mentioned above, in the method of the related art, there is a case where the prepared magnetic moment amount cannot be effectively used, and the most effective shimming cannot be realized within a range of the prepared magnetic moment amount.

The present invention has been made in consideration of the circumstances, and provides a technique for realizing effective shimming which uses a given magnetic moment amount to the maximum when redressing static magnetic field nonuniformity.

Solution to Problem

According to the present invention, when magnetic moment arrangement for correcting a nonuniform magnetic field distribution of a static magnetic field is calculated, an error magnetic field distribution is decomposed into eigenmode components obtained through singular value decomposition, a correction amount of a high-order eigenmode component is adjusted, and thus magnetic moment arrangement in which a usable magnetic moment amount prepared in advance is used to the maximum is calculated. An eigenmode may be divided into a low order and a high order according to, for example, the number of main coils.

Advantageous Effects of Invention

According to the present invention, it is possible to realize effective shimming by using a given magnetic moment amount to the maximum when redressing static magnetic field nonuniformity.

DESCRIPTION OF EMBODIMENTS

Figure 1:
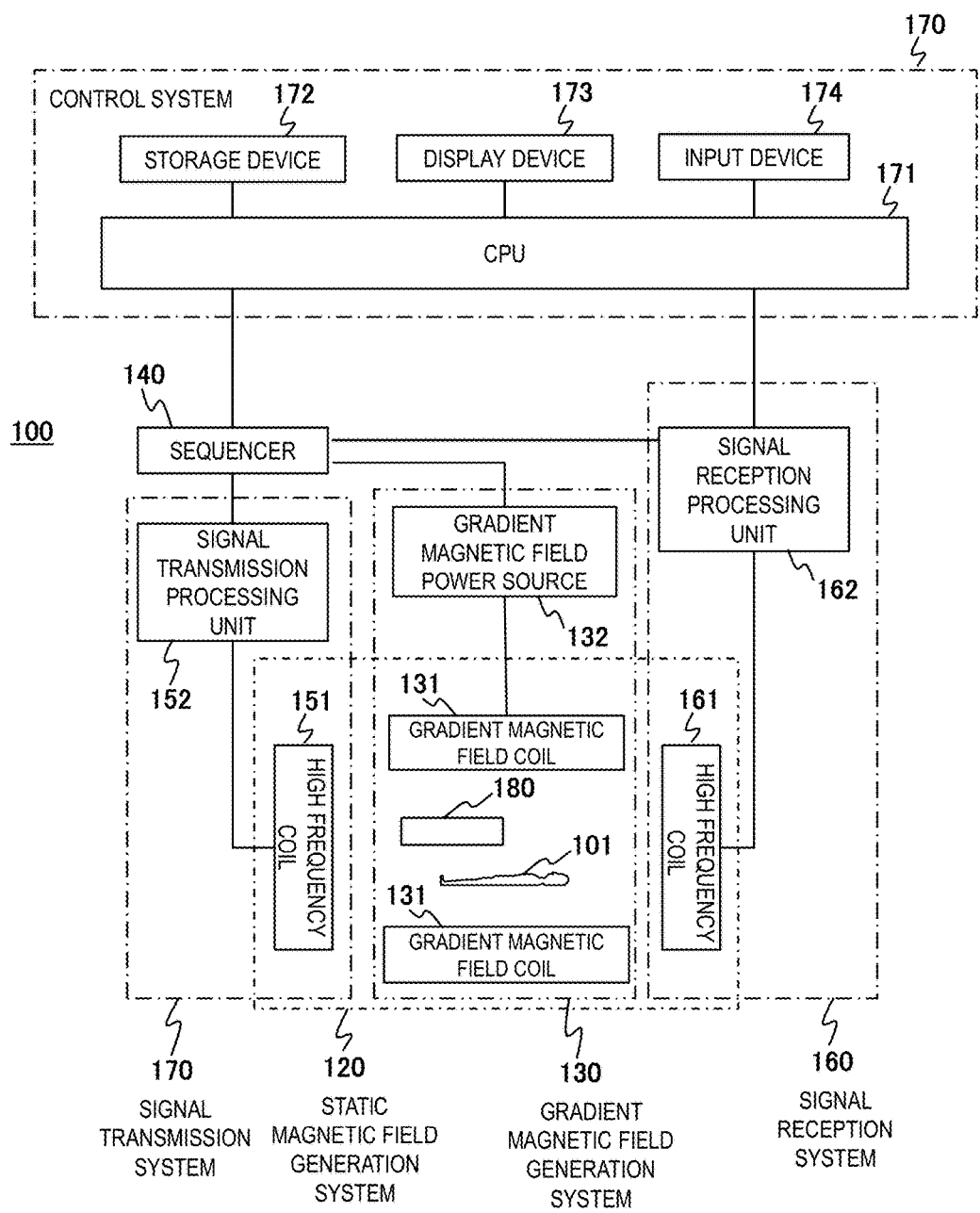
FIG. 1 is the entire configuration diagram of an MRI apparatus according to a first embodiment.

According to the present invention, there is provided a magnetic moment arrangement calculation method for magnetic field adjustment including measuring a magnetic field distribution of a predefined evaluation region in a magnetic field generation device including a magnetic field adjustment mechanism which adjusts a static magnetic field by using a magnetic moment disposed therein; calculating an error magnetic field distribution which is a difference between the measured magnetic field distribution and a predefined target magnetic field intensity of the evaluation region; decomposing the error magnetic field distribution into components of respective eigenmodes of a magnetic field generated by the magnetic field generation device, obtained through singular value decomposition; and combining correction of a component of a low-order mode with correction of a component of a high-order mode among the eigenmodes so as to calculate arrangement of the magnetic moment for approximately correcting the error magnetic field distribution, in which the low-order mode is an eigenmode group from the first of eigenmode numbers assigned to respective eigenmodes in the magnitude order of singular values to an eigenmode number specified by a first threshold value, in which the high-order mode is an eigenmode group with an eigenmode number more than the first threshold value, and in which a correction amount of the component of the high-order mode is smaller than a correction amount of the component of the low-order mode.

There is provided a magnetic moment arrangement calculation method for magnetic field adjustment, in which a computed magnetic moment amount which is a total magnetic moment amount based on the calculated arrangement of the magnetic moment is compared with a usable magnetic moment amount which is a usable magnetic moment amount prepared in advance, and the arrangement of the magnetic moment is repeatedly calculated by increasing a correction amount of the component of the high-order mode until the computed magnetic moment amount exceeds the usable magnetic moment amount.

There is provided a magnetic moment arrangement calculation method for magnetic field adjustment, in which the magnetic field generation device includes N (where N is an integer of 1 or more) main coils, and the first threshold value is defined according to the number N of main coils of the magnetic field generation device.

There is provided a magnetic moment arrangement calculation method for magnetic field adjustment, in which, among the respective eigenmodes, an identification number is assigned to an eigenmode in which a base of the eigenmode is axisymmetric with respect to a direction of a magnetic field generated by the magnetic field generation device and is plane-symmetric with respect to a plane which is orthogonal to the magnetic field direction in the magnitude order of singular values, and an eigenmode number which is one smaller than an eigenmode number of an N-th eigenmode from a small identification number is set as the first threshold value.

There is provided a magnetic moment arrangement calculation method for magnetic field adjustment, in which, when the arrangement of the magnetic moment is repeatedly calculated, a correction amount of components of the high-order mode is increased by increasing the number of times of combining the components of the high-order mode with each other.

There is provided a magnetic moment arrangement calculation method for magnetic field adjustment, in which the high-order mode is an eigenmode group from an eigenmode number one greater than the eigenmode number specified by the first threshold value to an eigenmode number specified by a second threshold value greater than the first threshold value.

There is provided a magnetic moment arrangement calculation method for magnetic field adjustment, in which the second threshold value is the maximum value of the eigenmode number, when the arrangement of the magnetic moment is repeatedly calculated, a predefined intensity coefficient is multiplied by the component of the eigenmode, and the intensity coefficient is determined so that a correction amount of components of the high-order mode is increased according to an increase of the number of times of repetition.

There is provided a magnetic moment arrangement calculation method for magnetic field adjustment, in which the magnetic field generation device includes N (where N is an integer of 1 or more) main coils, among the respective eigenmodes, an identification number is assigned to an eigenmode in which a base of the eigenmode is axisymmetric with respect to a direction of a magnetic field generated by the magnetic field generation device and is plane-symmetric with respect to a plane which is orthogonal to the magnetic field direction in the magnitude order of singular values, and an eigenmode number which is one smaller than an eigenmode number of an N-th eigenmode from a small identification number is set as the first threshold value, and, among the respective eigenmodes, an eigenmode number which is one smaller than an eigenmode number of a (N+1)-th eigenmode from a small identification number is set as the second threshold value.

There is provided a magnetic moment arrangement calculation method for magnetic field adjustment, in which, when the arrangement of the magnetic moment is calculated, an accommodation amount of the magnetic moment of the magnetic field adjustment mechanism is searched for as a restriction condition.

There is provided a magnetic field adjustment device including a magnetic field distribution measurement portion that measures a magnetic field distribution of a predefined evaluation region in a magnetic field generation device including a magnetic field adjustment mechanism which adjusts a static magnetic field by using a magnetic moment disposed therein; an arrangement computation portion that computes arrangement of the magnetic moment for correcting an error magnetic field distribution which is a difference between the measured magnetic field distribution and a predefined target magnetic field intensity of the evaluation region; and a low-order/high-order determination portion that divides each eigenmode of a magnetic field generated by the magnetic field generation device into a low-order mode which is an eigenmode group from the first of eigenmode numbers assigned to respective eigenmodes in the magnitude order of singular values to an eigenmode number specified by a first threshold value, and a high-order mode which is an eigenmode group with an eigenmode number more than the first threshold value, in which the arrangement computation portion decomposes the error magnetic field distribution into components of respective eigenmodes obtained through singular value decomposition, and combines correction of a component of a low-order mode with correction of a component of a high-order mode so as to calculate the arrangement of the magnetic moment for approximately correcting the error magnetic field distribution, and in which a correction amount of the component of the high-order mode is smaller than a correction amount of the component of the low-order mode.

There is provided a magnetic field adjustment device, in which the magnetic field generation device is a static magnetic field generation system of a magnetic resonance imaging apparatus.

There is provided a magnetic field adjustment device, in which the high-order mode is an eigenmode group from an eigenmode number one greater than the eigenmode number specified by the first threshold value to an eigenmode number specified by a second threshold value greater than the first threshold value.

There is provided a program causing a computer to function as a magnetic field distribution measurement portion that measures a magnetic field distribution of a predefined evaluation region in a magnetic field generation device including a magnetic field adjustment mechanism which adjusts a static magnetic field by using a magnetic moment disposed therein; an arrangement computation portion that computes arrangement of the magnetic moment for correcting an error magnetic field distribution which is a difference between the measured magnetic field distribution and a predefined target magnetic field intensity of the evaluation region; and a low-order/high-order determination portion that divides each eigenmode of a magnetic field generated by the magnetic field generation device into a low-order mode which is an eigenmode group from the first of eigenmode numbers assigned to respective eigenmodes in the magnitude order of singular values to an eigenmode number specified by a first threshold value, and a high-order mode which is an eigenmode group with an eigenmode number more than the first threshold value, in which the arrangement computation portion decomposes the error magnetic field distribution into components of respective eigenmodes obtained through singular value decomposition, and combines correction of a component of a low-order mode with correction of a component of a high-order mode so as to calculate the arrangement of the magnetic moment for approximately correcting the error magnetic field distribution, and in which a correction amount of the component of the high-order mode is smaller than a correction amount of the component of the low-order mode.

There is provided a program, in which the high-order mode is an eigenmode group from an eigenmode number one greater than the eigenmode number specified by the first threshold value to an eigenmode number specified by a second threshold value greater than the first threshold value.

First Embodiment

Hereinafter, with reference to the accompanying drawings, a description will be made of examples of embodiments of the present invention. Throughout all of the drawings for explaining the embodiments, constituent elements having the same functions are attached with same reference signs and will not be described repeatedly unless otherwise mentioned.

[MRI Apparatus Configuration]

First, the entire summary of an example of an MRI apparatus of the present embodiment will be described. FIG. 1 is a block diagram illustrating the entire configuration of an MRI apparatus 100 of the present embodiment. The MRI apparatus 100 of the present embodiment obtains a tomographic image of an object by using an NMR phenomenon, and, as illustrated in FIG. 1, includes a static magnetic field generation system 120, a gradient magnetic field generation system 130, a signal transmission system 150, a signal reception system 160, a control system 170, a sequencer 140, and a sensor 180.

The static magnetic field generation system 120 generates a uniform static magnetic field in a space around an object 101 in a direction orthogonal to a body axis of the object in a vertical magnetic field type, and generates a uniform static magnetic field in a body axis direction in a horizontal magnetic field type, and includes a permanent magnet type, normal conducting type, or superconducting type static magnetic field generation source disposed around the object 101. Hereinafter, in a coordinate system (apparatus coordinate system) of the MRI apparatus 100, a static magnetic field direction is set to a Z direction.

The gradient magnetic field generation system 130 includes gradient magnetic field coils 131 which are wound in three-axis directions of X, Y, and Z in a coordinate system (apparatus coordinate system) of the MRI apparatus 100, and a gradient magnetic field power source 132 which drives the gradient magnetic field coils, and applies gradient magnetic fields Gx, Gy and Gz in the three-axis directions of X, Y, and Z by driving the gradient magnetic field power source 132 for each of the gradient magnetic field coils 131 in response to a command from the sequencer 140. The gradient magnetic field intensity is changed by controlling a value of current flowing through the gradient magnetic field coils 131.

During imaging, for example, a slice surface is set for the object 101 by applying a gradient magnetic field pulse Gs in a direction which is orthogonal to the slice surface (imaging section), and echo signals are encoded with position information in respective directions by applying a gradient magnetic field pulse Gp and a gradient magnetic field pulse Gf in two remaining directions which are orthogonal to the slice surface and are orthogonal to each other. Hereinafter, in the present specification, a gradient magnetic field pulse which is applied in order to determine a slice surface will be referred to as a slice selection gradient magnetic field pulse, and a gradient magnetic field which is applied during reading of an echo signal in order to encode the echo signal with position information will be referred to as a reading gradient magnetic field pulse.

The signal transmission system 150 irradiates the object 101 with a high frequency magnetic field pulse (RF pulse) in order to cause nuclear magnetic resonance in an atomic nucleus spin of an atom forming a living body tissue of the object 101, and includes a signal transmission processing unit 152 provided with a high frequency oscillator (synthesizer), a modulator, and a high frequency amplifier, and a high frequency coil (signal transmission coil) 151 on the signal transmission side. The high frequency oscillator generates and outputs an RF pulse. The modulator amplitude-modulates the output RF pulse at a timing based on a command from the sequencer 140, and the high frequency amplifier amplifies the amplitude-modulated RF pulse, and supplies the RF pulse to the signal transmission coil 151 disposed near the object 101. The signal transmission coil 151 irradiates the object 101 with the supplied RF pulse.

The signal reception system 160 detects a nuclear magnetic resonance signal (an NMR signal or an echo signal) emitted due to nuclear magnetic resonance of atomic nucleus spins forming a living body tissue of the object 101, and includes a high frequency coil (signal reception coil) 161 on the signal reception side, and a signal reception processing unit 162 provided with a signal amplifier, a quadrature phase detector, and an A/D converter. The signal reception coil 161 is disposed near the object 101, and detects an echo signal which is caused by the object 101 in response to electromagnetic waves applied from the signal transmission coil 151. The detected echo signal which is amplified by the signal amplifier is divided into signals of two orthogonal systems by the quadratic phase detector at a timing based on a command from the sequencer 140, and the signals are converted into digital signals by the A/D converter so as to be transmitted to the control system 170.

The sequencer 140 repeatedly applies an RF pulse and a gradient magnetic field pulse according to a predetermined pulse sequence. The pulse sequence describes timings or intensities of a high frequency magnetic field pulse, a gradient magnetic field pulse, and signal reception, and is held in the control system 170 in advance. The sequencer 140 is operated in response to an instruction from the control system 170, and transmits various commands which are required to collect tomographic image data of the object 101, to the signal transmission system 150, the gradient magnetic field generation system 130, and the signal reception system 160.

The control system 170 performs control of the entire operation of the MRI apparatus 100, signal processing, various types of calculation such as image reconstruction, and display and preservation of a process result, and includes a CPU 171, a storage device 172, a display device 173, and an input device 174. The storage device 172 is formed of an internal storage device such as a hard disk, ROM, and PAM, and an external storage device such as an externally attached hard disk, an optical disc, and a magnetic disk. The display device 173 is a display device such as a CRT or a liquid crystal display. The input device 174 is an interface for inputting various pieces of control information regarding the MRI apparatus 100 or control information regarding processes performed by the control system 170, and includes, for example, a track ball or a mouse and a keyboard. The input device 174 is disposed near the display device 173. An operator inputs instructions and data which are required for various processes in the MRI apparatus 100 in an interactive manner via the input device 174 while viewing the display device 173.

The CPU 171 performs a program held in advance in the storage device 172 in response to an instruction which is input by the operator, so as to realize control of an operation of the MRI apparatus 100, and respective processes such as data processing in the control system 170, and functions thereof. For example, if data from the signal reception system 160 is input to the control system 170, the CPU 171 performs processes such as signal process and image reconstruction, displays a tomographic image of the object 101 as a result thereof on the display device 173, and stores the tomographic image in the storage device 172.

Some or all of the functions of the control system 170 may be realized by hardware such as an application specific integrated circuit (ASIC) or a field-programmable gate array (FPGA). Various pieces of data used for processing each function, and various pieces of data generated during processing are stored in the storage device 172.

The sensor 180 measures a static magnetic field generated by the static magnetic field generation system 120. The control system 170 is notified of a measurement result.

The signal transmission coil 151 and the gradient magnetic field coils 131 are provided to oppose the object 101 in a vertical magnetic field type, and to surround the object 101 in a horizontal magnetic field type, in a static magnetic field space of the static magnetic field generation system 120 into which the object 101 is inserted. The signal reception coil 161 is provided to oppose or surround the object 101.

Currently, an imaging target nuclide of the MRI apparatus, which is clinically popular, is a hydrogen nucleus (proton) which is a main constituent substance of the object 101. In the MRI apparatus 100, information regarding a spatial distribution of the proton density and information regarding a spatial distribution of the relaxation time of an excitation state are generated as an image so that a morphology or a function of the human head, abdomen, limbs, or the like is imaged in a two-dimensional or three-dimensional manner.

[Shimming Process]

As described above, the homogeneity of a static magnetic field influences image quality (distortion or luminance unevenness of an image, an SNR, and the like), and thus a spatially uniform static magnetic field is necessary in a region in which an NMR signal is measured. The homogeneity of a static magnetic field is expressed in the unit of parts per million (ppm: 1/1000000), and is calculated according to the following Equation (1), for example.

$$\text{Homogeneity} = \frac{B_{max} - B_{min}}{B_{ave}} * 10^6 [ppm] \quad (1)$$

Here, $B_{max}$ indicates the maximum magnetic field intensity in an evaluation space, $B_{min}$ indicates the minimum magnetic field intensity in the evaluation space, and $B_{ave}$ indicates the average magnetic field intensity in the evaluation space. As the evaluation space, typically, a surface of a sphere or an ellipse is designated.

In a case of an MRI apparatus used in clinical practice at the average magnetic field intensity of 1.5 T, the homogeneity of about 3 ppm in a surface of a sphere with the diameter of 400 mm is required. In other words, a difference between $B_{max}$ and $B_{min}$ in Equation (1) is required to be equal to or less than about 4.5 µT in the surface of the sphere with the diameter of 400 mm.

In order to realize such a static magnetic field space, the MRI apparatus 100 performs work of reducing an error magnetic field, called shimming. The error magnetic field is a difference between a magnetic field measured in an evaluation space and a desired magnetic field. In the shimming, the error magnetic field is reduced by disposing a substance (hereinafter, simply referred to as magnetic moment) having a magnetic moment of a predetermined magnitude, such as an iron piece at a predetermined position. Thus, in the shimming, it is necessary to determine a magnetic moment arrangement position and arrangement amount (hereinafter, referred to as magnetic moment arrangement) which cause the error magnetic field to be effectively reduced.

[Static Magnetic Field Generation System]

FIGS. 2(a) and 2(b) illustrate an outline of a representative structure of the static magnetic field generation system 120 of the horizontal magnetic field type MRI apparatus 100. FIG. 2(a) is an XY sectional view, and FIG. 2(b) is an AA sectional view in FIG. 2(a).

The static magnetic field generation system 120 includes a superconducting magnet 121; a container 122 for disposing a magnetic moment; magnetic moments 123 such as iron pieces; and main coils 125 forming the superconducting magnet 121. The reference numeral 124 indicates an evaluation space (evaluation region).

The static magnetic field generation system 120 of the present embodiment is assumed to have N main coils 125. Here, N is an integer of 1 or more.

The container 122 is a magnetic field adjustment mechanism in which the magnetic moments 123 are disposed, and thus a static magnetic field is adjusted. Thus, the container 122 includes a plurality of pockets into which the magnetic moments 123 are inserted.

As described above, in the shimming, the magnetic moments 123 of an appropriate number are disposed at appropriate positions in the container 122, and thus a static magnetic field distribution in the evaluation space 124 is adjusted (corrected). The homogeneity of a static magnetic field which can be achieved is determined depending on the accuracy of the shimming, that is, the propriety of arrangement of the magnetic moments 123. Therefore, determination of an amount of magnetic moments for arrangement in the respective pockets of the container 122 is important. Hereinafter, determination of an amount of magnetic moments disposed in the respective pockets will be referred to as determination of magnetic moment arrangement.

[Shimming Using Singular Value Decomposition]

A description will be made of a method of determining magnetic moment arrangement by using singular value decomposition according to the technique disclosed in the above PTL 1. In this method, magnetic moment arrangement which generates a magnetic field distribution for canceling an error magnetic field from a nonuniform magnetic field distribution (error magnetic field) of a static magnetic field is obtained. This computation corresponds to an inverse problem of obtaining magnetic moment arrangement on the basis of a magnetic field. In this method, truncated singular value decomposition is used to solve the inverse problem.

The singular value decomposition is applied to a response matrix A for a magnetic field of the evaluation space 124 on the basis of a current potential on the container 122, and, as a result, a base $v_j$ of a current potential distribution on the container 122 and a base $u_j$ of a magnetic field distribution on the evaluation space 124 are obtained. The two bases $v_j$ and $u_j$ have a relationship of the following Equation (2).

$$\lambda_j \cdot u_j = A \cdot v_j \quad (2)$$

Here, $\lambda_j$ is a singular value, and indicates the magnitude of a magnetic field generated by a current potential per unit. The subscript j is a number assigned in the magnitude order of singular values $\lambda_j$ and is called an eigenmode number or an order of an eigenmode. In addition, $u_j$ indicates a base of a magnetic field distribution obtained through singular decomposition of the response matrix A. Further, $u_j$ and $v_j$ are vectors.

In other words, Equation (2) correlates a magnetic field distribution on the container 122 with a magnetic field distribution on the surface of the evaluation space 124. The current potential may be converted into magnetic moment arrangement.

Figure 3:
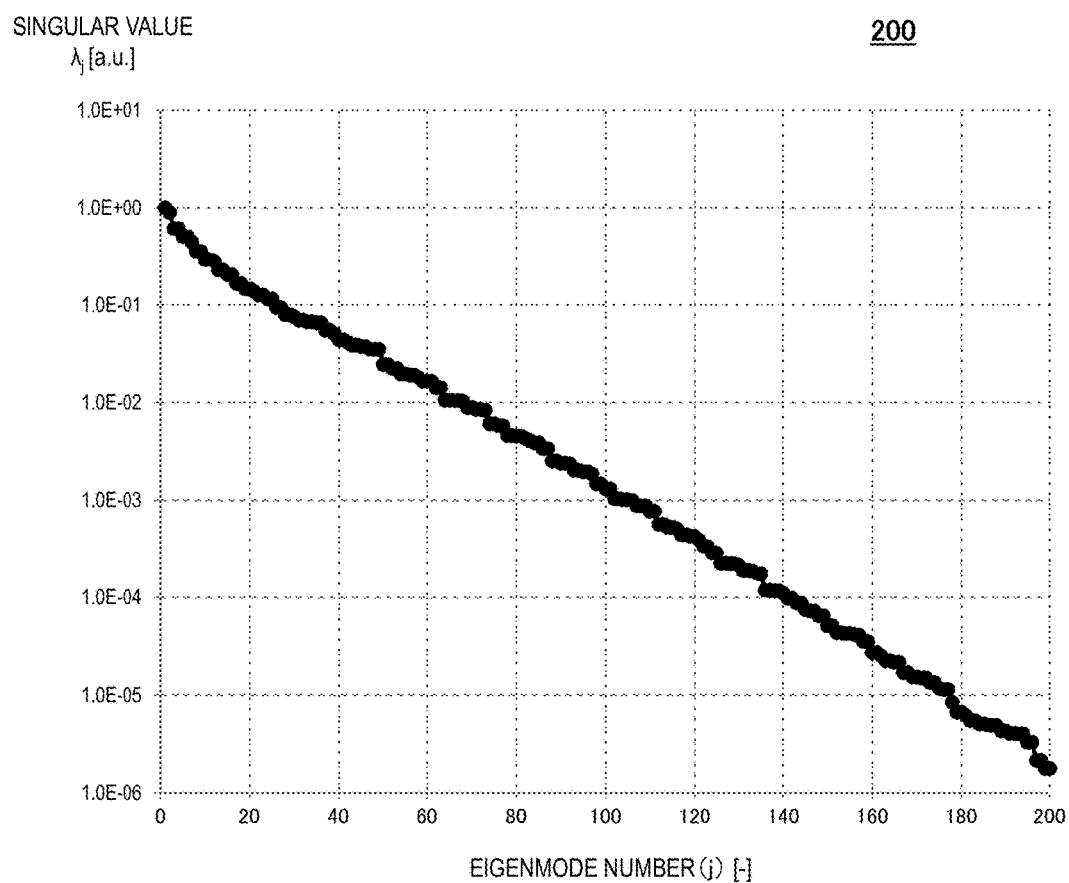
FIG. 3 is a graph of a singular value distribution according to the first embodiment.

FIG. 3 illustrates a distribution of the singular value $\lambda_j$ (singular value distribution) 200 for each eigenmode number j with respect to a magnetic field generated by the static magnetic field generation system 120 of the MRI apparatus 100. As described above, the eigenmode number j is a number assigned in the magnitude order of the singular value $\lambda_j$, and thus the singular value $\lambda_j$ is reduced as the eigenmode number j increases. The singular value $\lambda_j$ for each eigenmode number j is defined on the basis of a positional relationship between the container 122 and the evaluation space 124.

A shimming target is an error magnetic field corresponding to a difference between a magnetic field (measured magnetic field) measured in the evaluation region 124 and a desired magnetic field distribution. The error magnetic field may be decomposed into and expressed by components with eigenmode numbers. An intensity $C_j$ of a component with each eigenmode number j of an error magnetic field $B_e$ is calculated according to the following Equation (3).

$$C_j = B_e \cdot u_j \quad (3)$$

In other words, if inner product between the error magnetic field $B_e$ and the base $u_j$ of a magnetic field distribution is taken, the intensity (hereinafter, referred to as eigenmode intensity) $C_j$ of a component with the eigenmode number j is obtained. In addition, $B_e$ is a vector. Obtaining the intensity $C_j$ of a component with the eigenmode number j by taking inner product between the error magnetic field $B_e$ and the base $u_j$ of a magnetic field distribution is referred to as decomposing the error magnetic field distribution $B_e$ into eigenmode components.

Figure 4:
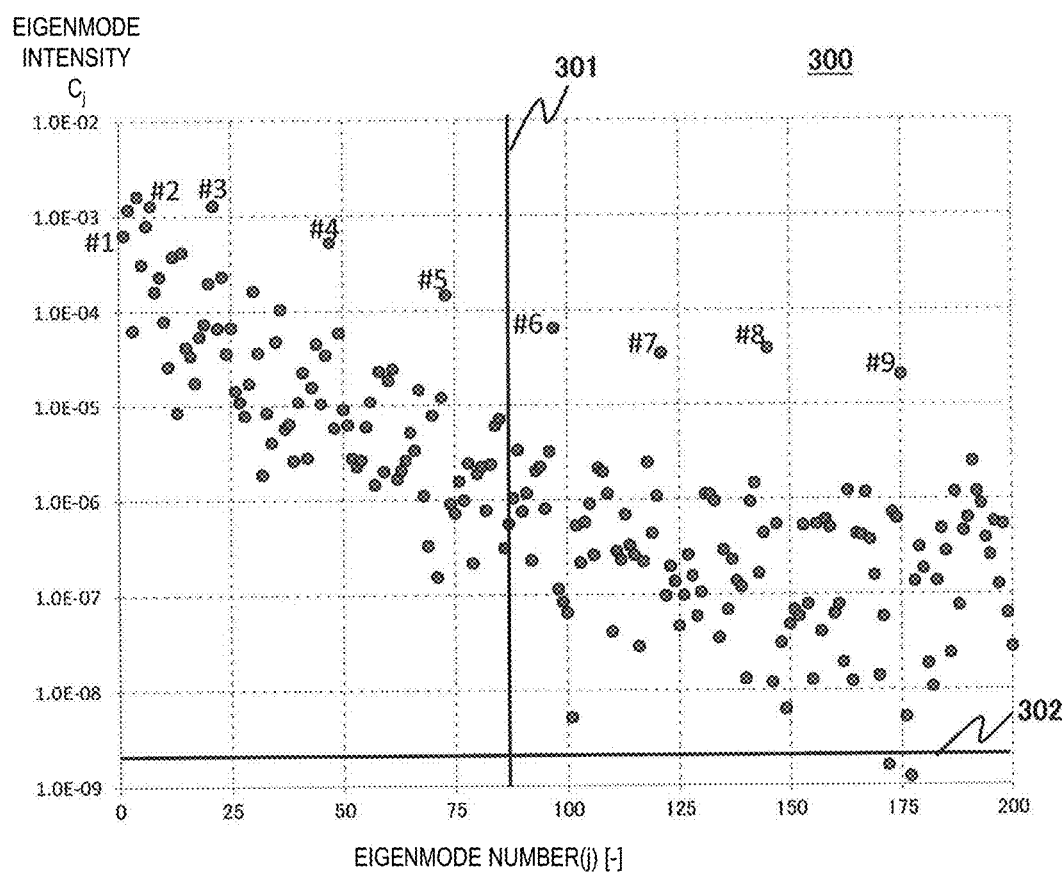
FIG. 4 is a graph of an eigenmode distribution of an error magnetic field according to the first embodiment.

FIG. 4 illustrates a distribution 300 of the eigenmode intensity $C_j$ of the error magnetic field $B_e$ for each eigenmode number j. Hereinafter, this distribution will be referred to as an eigenmode distribution 300. Each point (the eigenmode intensity $C_j$ with the eigenmode number j) in this distribution will be simply referred to as an eigenmode.

In order to completely remove the error magnetic field $B_e$, it is necessary to make the eigenmode intensities $C_j$ which are components with all of the eigenmode numbers j illustrated in FIG. 4 zero. However, a large number of magnetic moments 123 are required to completely remove the error magnetic field $B_e$. This is not realistic since a size of the container 122 is finite. Thus, it is necessary to take into consideration restriction of arrangement position and an amount of the magnetic moments 123 due to the container 122 and then to calculate a solution to the most effective magnetic moment arrangement, that is, a solution causing the best homogeneity of a static magnetic field.

Generally, in the shimming, correction is performed in which a small eigenmode number j is preferentially selected, and the eigenmode intensity $C_j$ approaches zero. This is because, as is clear from FIG. 3, a component with a smaller eigenmode number j has a greater singular value $\lambda_j$, and a magnetic field which can be corrected per magnetic moment becomes larger.

Specifically, as illustrated in FIG. 4, a threshold value 301 of the maximum value of the eigenmode number j which is a correction target is set, and magnetic moment arrangement is determined in which the eigenmode intensity $C_j$ with the eigenmode number j which is equal to or smaller than the threshold value 301 is equal to or less than a threshold value 302 of the eigenmode intensity.

As described above, in the technique disclosed in PTL 1, correction targets are eigenmode numbers j which are equal to or less than the threshold value 301, and shimming computation is performed so that all of the eigenmode intensities $C_j$ with the correction target eigenmode numbers j are equal to or less than the threshold value 302.

As the number of correction target eigenmodes is increased, more magnetic moments are necessary, and thus an error magnetic field is corrected. Thus, it is necessary to define a correction target eigenmode so that the maximum correction effect can be achieved within a range of a magnetic moment amount which can be used. However, as described above, in the method disclosed in PTL 1, a usable magnetic moment amount may remain. In other words, a necessary magnetic moment amount may rapidly change between the eigenmode number j and the eigenmode number j+1, and thus there may be a case where a necessary magnetic moment amount is smaller than a usable magnetic moment amount in the eigenmode number j, and is deficient in the next eigenmode number j+1, depending on a method of selecting the correction target eigenmode number j.

Figure 5:
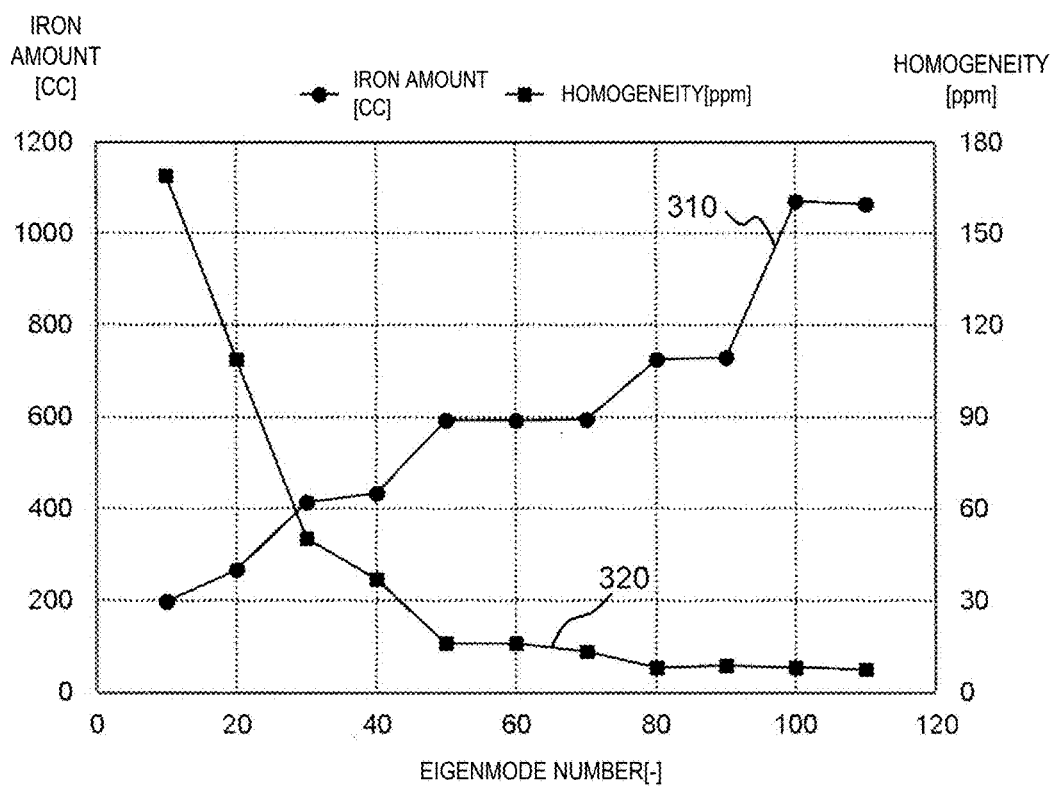
FIG. 5 is a graph for explaining a change in an amount of used iron and a change in homogeneity during shimming.
Figure 6:
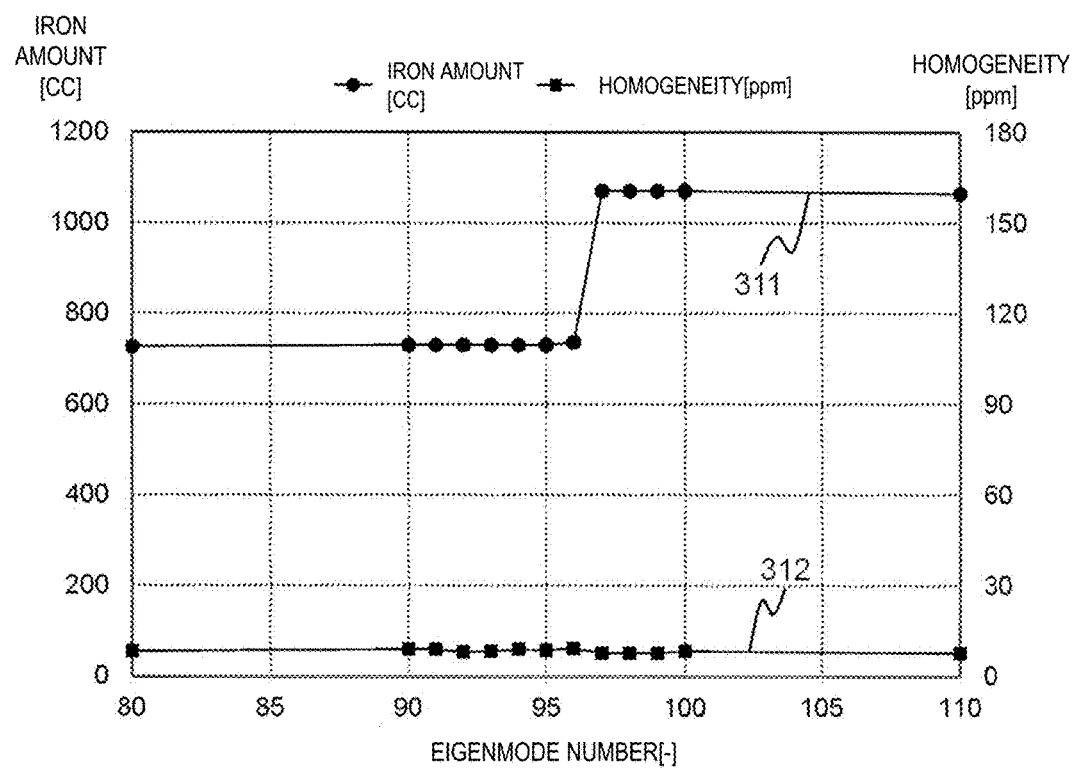
FIG. 6 is a graph for explaining a change in an amount of used iron and a change in homogeneity during shimming.

This will be described by using actual examples. FIGS. 5 and 6 are graphs as actual examples illustrating a relationship between a magnetic moment amount and the homogeneity [ppm] when the threshold value 301 (the maximum value of an eigenmode number which is a correction target) is changed according to the method disclosed in PTL 1.

FIG. 5 is a graph 310 illustrating a change in an iron amount and a graph 320 illustrating a change in the homogeneity when the threshold value 301 is changed from 10 to 110 in the unit of 10. FIG. 6 is a graph 311 illustrating a change in an iron amount and a graph 312 illustrating a change in the homogeneity when the threshold value 301 is changed from 90 to 100 in the unit of 1.

In each graph of FIGS. 5 and 6, a magnetic moment amount is converted into and displayed as an iron amount [cc]. A magnetic moment amount is converted into an iron amount with the magnetic moment of 123 of saturated pure iron (2.15 T) as 1.711 $Am^2/cc$.

As can be seen from FIGS. 5 and 6, a change in a necessary magnetic moment amount is not continued but stepped. Therefore, there is a case where there is no threshold value 301 at which the whole of a usable magnetic moment amount is used.

As a specific example, a case where a usable iron amount is 1000 cc is assumed. In this case, if the maximum value of the eigenmode number j which is a correction target, that is, the threshold value 301 is 96, an iron amount used for the correction is about 737 cc, and thus does not reach the whole of a usable iron amount of 1000 cc. If the threshold value 301 is increased by 1 and to 97, an iron amount required for correction is about 1070 cc, and thus exceeds the usable iron amount of 1000 cc.

As mentioned above, in the method of the related art in which correction is sequentially performed from the intensity with a low-order eigenmode number, it is hard to effectively completely use a prepared and usable magnetic moment amount. In other words, in the method of the related art, the best static magnetic field homogeneity is not achieved under restriction of a given magnetic moment amount.

[Control System]

In the present embodiment, in shimming, each eigenmode of an error magnetic field distribution is divided into a low-order region and a high-order region with an eigenmode number as a reference, an eigenmode (low-order mode) of the low-order region is corrected to be equal to or less than a predetermined threshold value in the same manner as in the related art, and an eigenmode (high-order mode) of the high-order region is corrected within a range of a usable magnetic moment amount as much as possible.

Figure 7:
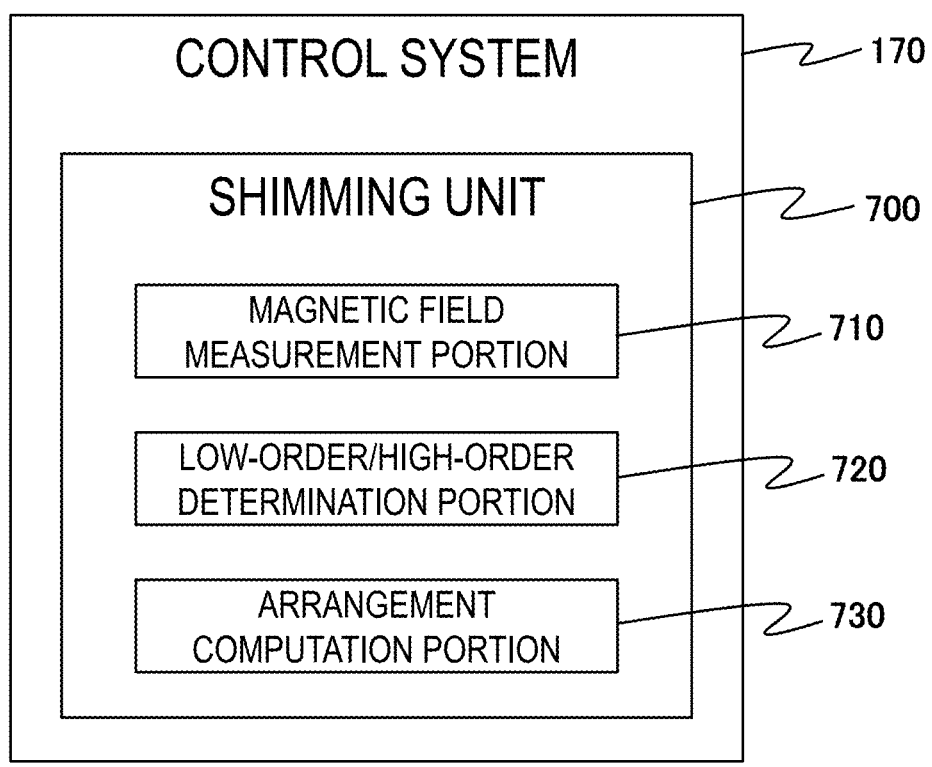
FIG. 7 is a functional block diagram of a control system according to the first embodiment.
Figure 8:
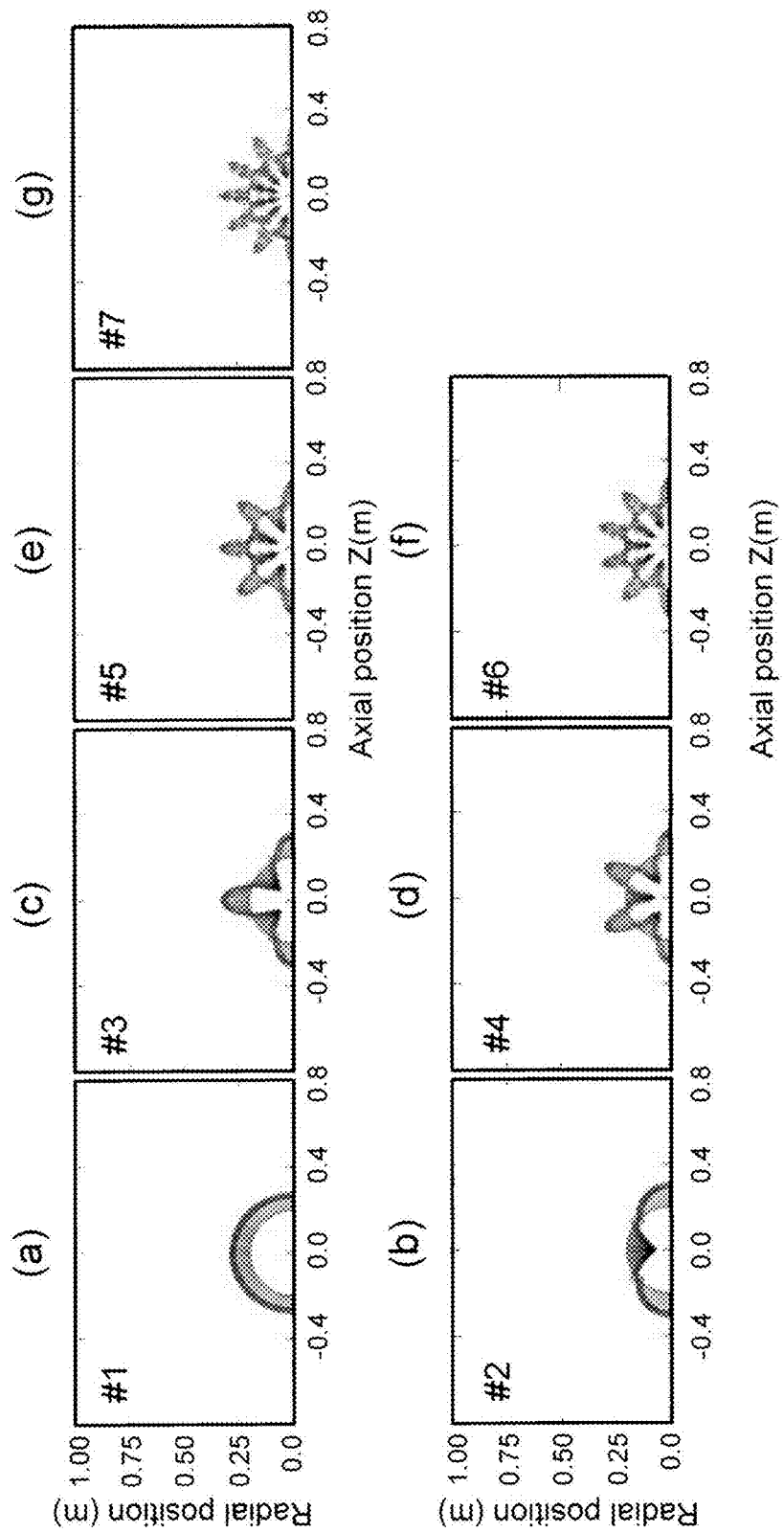
FIGS. 8(a) to 8(g) are diagrams for explaining shapes of symmetric bases in a case where the number of main coils is six.

In order to realize this, the control system 170 of the present embodiment includes a shimming unit 700 performing shimming as illustrated in FIG. 7 as a function related to a shimming process. The shimming unit 700 performs magnetic moment arrangement computation until a magnetic moment amount $V_{set}$ which is prepared in advance is completely used while increasing a correction amount in a high-order mode. Thus, the shimming unit 700 includes a magnetic field measurement portion 710 which actually measures a magnetic field distribution of the evaluation space 124, a low-order/high-order determination portion 720 which determines upper limit eigenmode numbers j in a low-order mode and a high-order mode, and an arrangement computation portion 730 which determines magnetic moment arrangement.

[Magnetic Field Measurement Portion]

The magnetic field measurement portion 710 of the present embodiment measures a magnetic field distribution (measured magnetic field distribution) $B_m$ of the predefined evaluation region 124 in the static magnetic field generation system 120. The measurement is performed by the sensor 180, and the magnetic field measurement portion 710 receives a measurement result from the sensor 180.

[Low-Order/High-Order Determination Portion]

The low-order/high-order determination portion 720 of the present embodiment obtains the base $u_j$ for specifying an eigenmode of the static magnetic field generation system 120, and divides the base into correction ranges depending on the number N of main coils 125. The base is divided into a correction range in a low-order mode in which the eigenmode intensity $C_j$ is corrected to be equal to or less than a predetermined threshold value in the same manner as in the related art, and a correction range in a high-order mode in which correction is performed within a range of a usable magnetic moment amount as much as possible. As a division result, an upper limit eigenmode number j for each of the correction ranges in a low-order mode and a high-order mode is output. Various pieces of information required for a low-order/high-order determination process are stored in the storage device 172 in advance as an apparatus information.

Specifically, first, the low-order/high-order determination portion 720 of the present embodiment divides each eigenmode of a magnetic field generated by a magnetic field generation device (static magnetic field generation system 120) into a low-order mode which is an eigenmode group from the first of the eigenmode numbers assigned to respective eigenmodes in the magnitude order of singular values to an eigenmode number specified by a first threshold value $T_L$, and a high-order mode which is an eigenmode group from an eigenmode number one greater than the eigenmode number specified by the first threshold value $T_L$ to an eigenmode number specified by a second threshold value $T_H$ greater than the first threshold value $T_L$.

In other words, the first threshold value $T_L$ is an upper limit value of the eigenmode number j of the eigenmode group included in the low-order mode. The second threshold value $T_H$ is an upper limit value of the eigenmode number j of the eigenmode group included in the high-order mode.

The low-order/high-order determination portion 720 of the present embodiment defines such first threshold value and second threshold value depending on the number N of main coils 125 included in the magnetic field generation system 120.

Specifically, among respective eigenmodes, an identification number #p is assigned to an eigenmode in which the base $u_j$ of the eigenmode is axisymmetric with respect to a direction of a magnetic field generated by the magnetic field generation system 120 and is plane-symmetric with respect to a plane which is orthogonal to the magnetic field direction in the magnitude order of singular values, and an eigenmode number (j−1) which is one smaller than the eigenmode number j of an N-th eigenmode from a small identification number #p is set as the first threshold value $T_L$. Among the respective eigenmodes, an eigenmode number (j−1) which is one smaller than the eigenmode number j of a (N+1)-th eigenmode from the small identification number #p is set as the second threshold value $T_H$.

Hereinafter, a base of an eigenmode which is axisymmetric with respect to an axis in the magnetic field direction and is plane-symmetric with respect to a plane which is orthogonal to the magnetic field direction will be referred to as a symmetric base $u_j$. As described above, in the present embodiment, the magnetic field direction is set to a Z axis direction. Therefore, the symmetric base $u_j$ is the base $u_j$ which is axisymmetric with respect to a Z axis, and is plane-symmetric with respect to an XY plane.

The identification number #p is assigned to the eigenmode intensity $C_j$ with the eigenmode number j corresponding to the symmetric base $u_j$ in the error magnetic field $B_e$ illustrated in FIG. 4.

For example, FIGS. 8(a) to 8(g) illustrate shapes of the symmetric bases $u_j$ with respective identification numbers #p in a case where the number N of main coils 125 is six. FIGS. 8(a) to 8(g) illustrate examples of a case where the number N of main coils 125 of the superconducting magnet 121 is six. Each figure illustrates a set of vectors of respective points of the base in the evaluation space. The identification numbers #1 to #7 written in FIGS. 8(a) to 8(g) correspond to the numbers written in the eigenmode distribution illustrated in FIG. 4. In the shapes of the respective symmetric bases in FIGS. 8(a) to 8(g), each transverse axis expresses a distance (position) (Axial position) in the Z axis direction, and each longitudinal axis expresses a radial distance (Radial position) with the Z axis as a starting point on the XY plane.

In the present embodiment, as described above, a direction of a magnetic field generated by the static magnetic field generation system 120 is the Z axis direction. Among magnetic fields forming the magnetic field distribution, a magnetic field caused by the main coils 125 is axisymmetric with respect to the Z axis and is plane-symmetric with respect to the XY plane on the basis of a shape thereof.

Therefore, the base $u_j$ of an eigenmode which is axisymmetric in the direction of a magnetic field generated by the magnetic field generation system 120 and is plane-symmetric with respect to a plane which is orthogonal to the magnetic field direction is the base $u_j$ corresponding to a magnetic field generated by each main coil 125.

As can be seen from the fact that each symmetric base $u_j$ is Z axis-symmetric and XY plane-symmetric, the intensity thereof is defined depending on a shape and a position of the main coil 125, and does not depend on arrangement of the magnetic moment 123 in the container 122.

In many superconducting magnets, in a case where the number of reading main coils is N, the intensity of an eigenmode corresponding to the symmetric base $u_j$ with the identification number #p which is less than N is designed to be reduced. Thus, generally, shimming can be performed in a relatively small magnetic moment amount up to an eigenmode corresponding to the symmetric base $u_j$ with the identification number #p which is less than N. However, in a case where shimming is performed on correction target eigenmodes including the symmetric bases $u_j$ of N or more, a large magnetic moment amount is necessary.

Therefore, the number N of main coils is used as a reference, and the symmetric base $u_j$ with the identification number #p of N is used as a threshold value for dividing an eigenmode into a low-order mode and a high-order mode. In other words, in the present embodiment, the low-order/high-order determination portion 720 determines division into a low-order mode and a high-order mode depending on the number of main coils 125 (referred to as the number of main coils) of the superconducting magnet 121.

Therefore, the low-order/high-order determination portion 720 of the present embodiment determines a low-order mode and a high-order mode by using the symmetric base $u_j$. In other words, the symmetric base $u_j$ with the identification number #p corresponding to number N of main coils is used as a threshold value for dividing an eigenmode into a low-order mode and a high-order mode.

Specifically, a value of (j−1) obtained by subtracting 1 from the subscript (eigenmode number j) of the symmetric base $u_j$ with the identification number #N is set as an upper limit value $T_L$ of a low-order mode. Specifically, a value of (j−1) obtained by subtracting 1 from the subscript (eigenmode number j) of the symmetric base with the identification number #(N+1) is set as an upper limit value $T_H$ of a high-order mode.

The low-order/high-order determination portion 720 of the present embodiment determines the upper limit value $T_L$ of a low-order mode. In other words, an eigenmode with the eigenmode number j less than the upper limit value $T_L$ is set as a low-order eigenmode. The upper limit value of a low-order mode is an eigenmode number, that is, j−1, one smaller than the eigenmode number j corresponding to an N-th identification number #p in ascending order among identification numbers #p of a specific eigenmode number.

On the other hand, the low-order/high-order determination portion 720 also determines the upper limit value $T_H$ of a high-order mode. The upper limit value $T_H$ of a high-order mode is an eigenmode number, that is, j−1, one smaller than the eigenmode number j corresponding to a (N+1)-th identification number #p.

This will be described in detail by exemplifying the eigenmode distribution 300 illustrated in FIG. 4. The number N of main coils 125 of the superconducting magnet used to measure the eigenmode distribution 300 is six. The eigenmode number j corresponding to the identification number #6 is 97. The eigenmode number j corresponding to the identification number #7 is 121. In this case, the upper limit value $T_L$ of a low-order mode is determined as 97−1, that is, 96. The upper limit value $T_H$ of a high-order mode is determined as 121−1, that is, 120.

Through the above-described process, the low-order/high-order determination portion 720 of the present embodiment divides an eigenmode into two regions such as a low-order mode and a high-order mode on the basis of a shape of the superconducting magnet 121.

Figure 2:
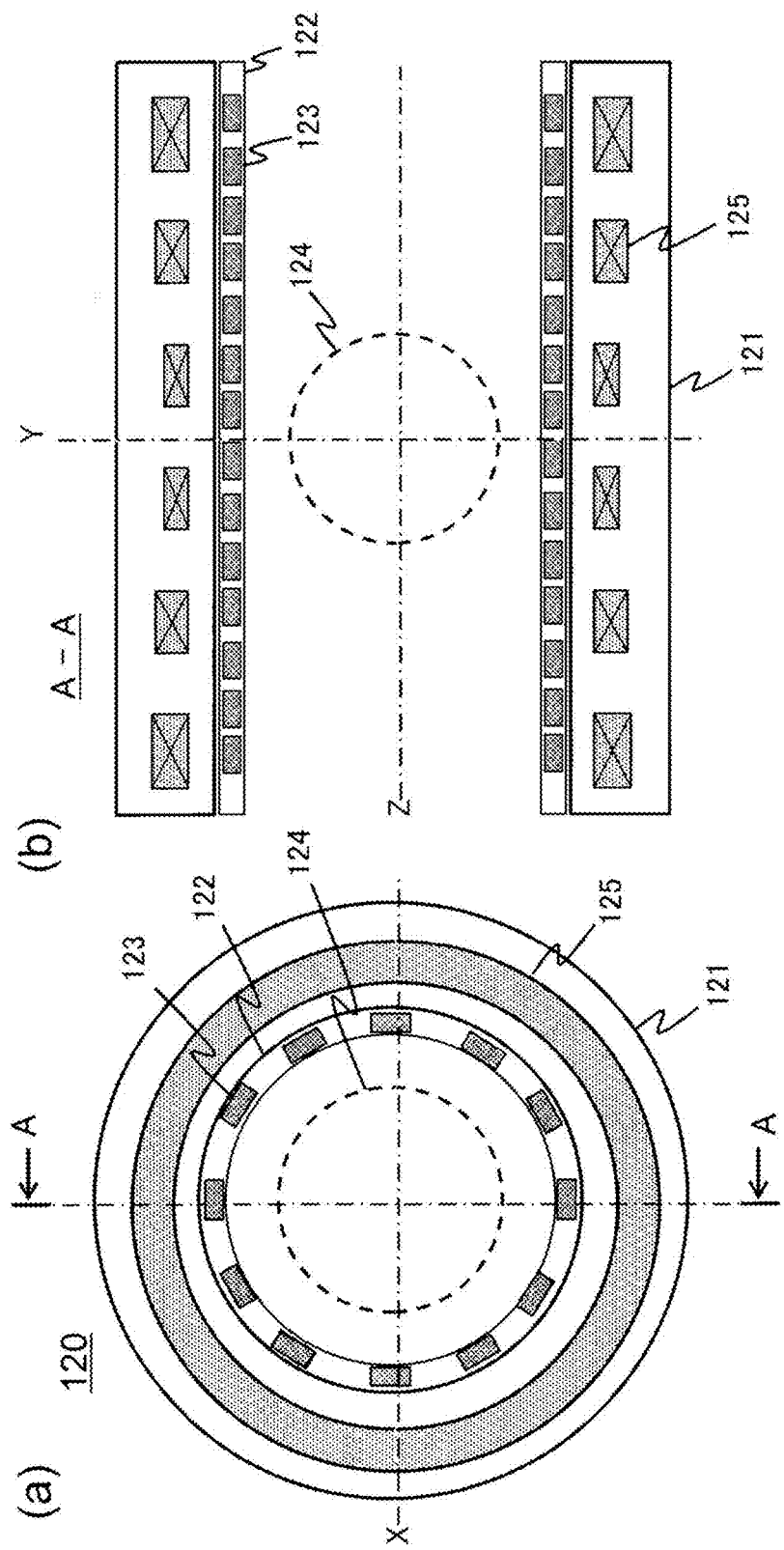
FIG. 2(a) is an XY sectional view of a static magnetic field generation system 120 of the MRI apparatus according to the first embodiment.
FIG. 2(b) is an AA sectional view in FIG. 2(a).

Directions along the X, Y and Z axes are the same as illustrated in FIG. 2. In other words, a magnetic field direction of the magnet of the MRI apparatus is along the Z axis, and other axes are the X and Y axes. FIG. 2 corresponds to a horizontal magnetic field type MRI apparatus, but is defined in the same manner for a vertical magnetic field type MRI apparatus.

A method of determining a low-order mode and a high-order mode is not limited thereto. For example, the first threshold value and/or the second threshold value may be designated by a user.

[Arrangement Computation Portion]

The arrangement computation portion 730 computes magnetic moment arrangement for correcting the error magnetic field distribution $B_e$ which is a difference between a measured magnetic field distribution (measured magnetic field distribution $B_m$) and a predefined target magnetic field intensity $B_{Target}$ of the evaluation region 124. Determining magnetic moment arrangement is to determine an amount of magnetic moments for arrangement in the respective pockets of the container 122. In other words, a magnetic moment amount of each pocket is determined.

When magnetic moment arrangement is computed, the arrangement computation portion 730 of the present embodiment decomposes the error magnetic field distribution $B_e$ into components of respective eigenmodes of a magnetic field generated by the magnetic field generation device (static magnetic field generation system 120), obtained through singular value decomposition, combines correction of a low-order mode component with correction of a high-order mode component, and calculates the magnetic moment arrangement for approximately correcting the error magnetic field distribution. In this case, a correction amount of the high-order mode component is made smaller than a correction amount of the low-order mode component.

In this case, the arrangement computation portion 730 of the present embodiment compares a computed magnetic moment amount $V_{sum}$ which is a total of magnetic moment amounts based on the calculated magnetic moment arrangement with a usable magnetic moment amount $V_{set}$ which is a usable magnetic moment amount prepared in advance, and repeatedly calculates magnetic moment arrangement by increasing a correction amount of the high-order mode component until the computed magnetic moment amount $V_{sum}$ exceeds the usable magnetic moment amount $V_{set}$.

The arrangement computation portion 730 of the present embodiment increases the number of times of combining components of an eigenmode group divided as a high-order mode with each other, and thus increases a correction amount of the components of the eigenmode group divided as a high-order mode, when the magnetic moment arrangement is repeatedly calculated.

In the present embodiment, when magnetic moment arrangement is calculated, the arrangement computation portion 730 searches for an optimal solution with a magnetic moment accommodation amount of each pocket of the container 122 which is a magnetic field adjustment mechanism as a restriction condition.

[Shimming Process]

Figure 9:
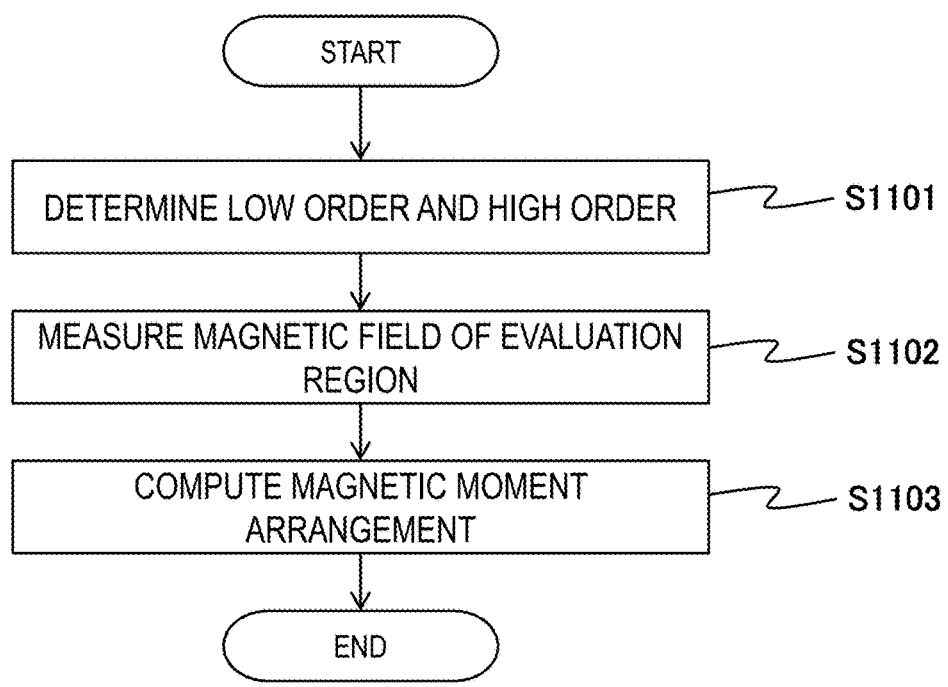
FIG. 9 is a flowchart illustrating a shimming process according to the first embodiment.

Hereinafter, a description will be made of details of a shimming process performed by each portion of the shimming unit 700 of the present embodiment along a flow of the process with reference to a flowchart of FIG. 9.

First, the low-order/high-order determination portion 720 performs a low-order/high-order determination process of dividing an eigenmode into a low-order mode and a high-order mode by using the eigenmode (base $u_j$) and the number N of main coils 125 of the static magnetic field generation system 120 (step S1101). This process may be performed at any timing before a magnetic moment arrangement computation process is performed.

The magnetic field distribution measurement portion measures a magnetic field distribution (measured magnetic field distribution) $B_m$ of the evaluation space (evaluation region) 124 (step S1102).

The arrangement computation portion 730 performs a magnetic moment arrangement computation process of computing magnetic moment arrangement with a magnetic moment accommodation amount of each pocket of the container 122 as a restriction condition by using the measured magnetic field distribution $B_m$, the first threshold value $T_L$ for specifying a low-order mode, and the second threshold value $T_H$ for specifying a high-order mode (step S1103). In the magnetic moment arrangement computation process, an optimal solution of the magnetic moment arrangement is searched for while increasing the number of times of combining components of an eigenmode group divided as a high-order mode with each other, and the magnetic moment arrangement is computed.

[Low-Order/High-Order Determination Process]

Figure 10:
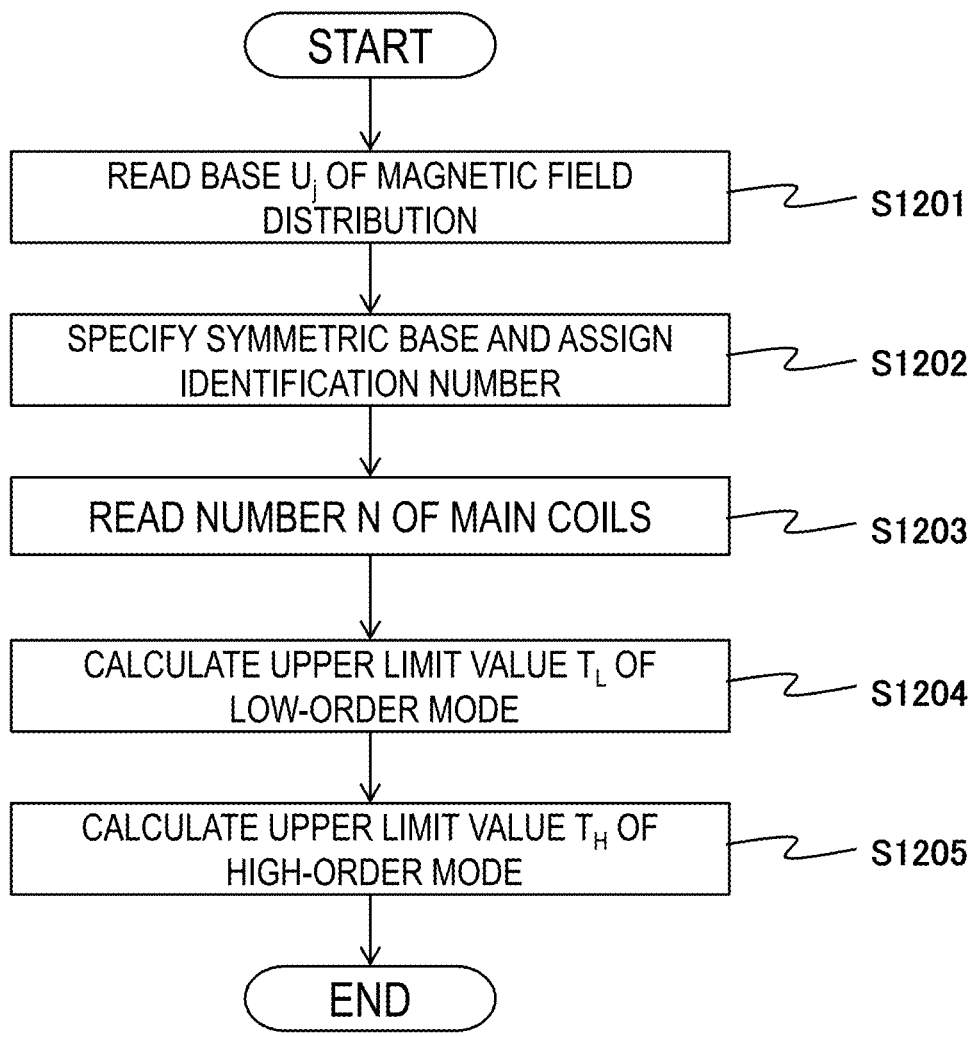
FIG. 10 is a flowchart illustrating a low-order/high-order determination process according to the first embodiment.

A description will be made of a flow of the low-order/high-order determination process performed by the low-order/high-order determination portion 720 with reference to the process flow in FIG. 10.

First, the low-order/high-order determination portion 720 reads the bases $u_j$ of a magnetic field distribution obtained through singular value decomposition of the response matrix A (step S1201). The symmetric base $u_j$ is specified among the read bases $u_j$. The identification number #p is assigned to the symmetric base $u_j$ in the order (the magnitude order of singular values) of the eigenmode number j of a corresponding eigenmode as described above (step S1202).

The low-order/high-order determination portion 720 reads the number N of main coils 125 (step S1203). The number of main coils is held in advance as apparatus information or the like.

Next, the low-order/high-order determination portion 720 calculates the upper limit value $T_L$ of a low-order mode according to the above-described method by using the subscript j of the base with the identification number #p of N in the symmetric base $u_j$ (step S1204). The low-order/high-order determination portion 720 calculates the upper limit value $T_H$ of a high-order mode according to the above-described method by using the subscript j of the base with the identification number #p of N+1 in the symmetric base $u_j$ (step S1205).

[Arrangement Computation Process]

Figure 11:
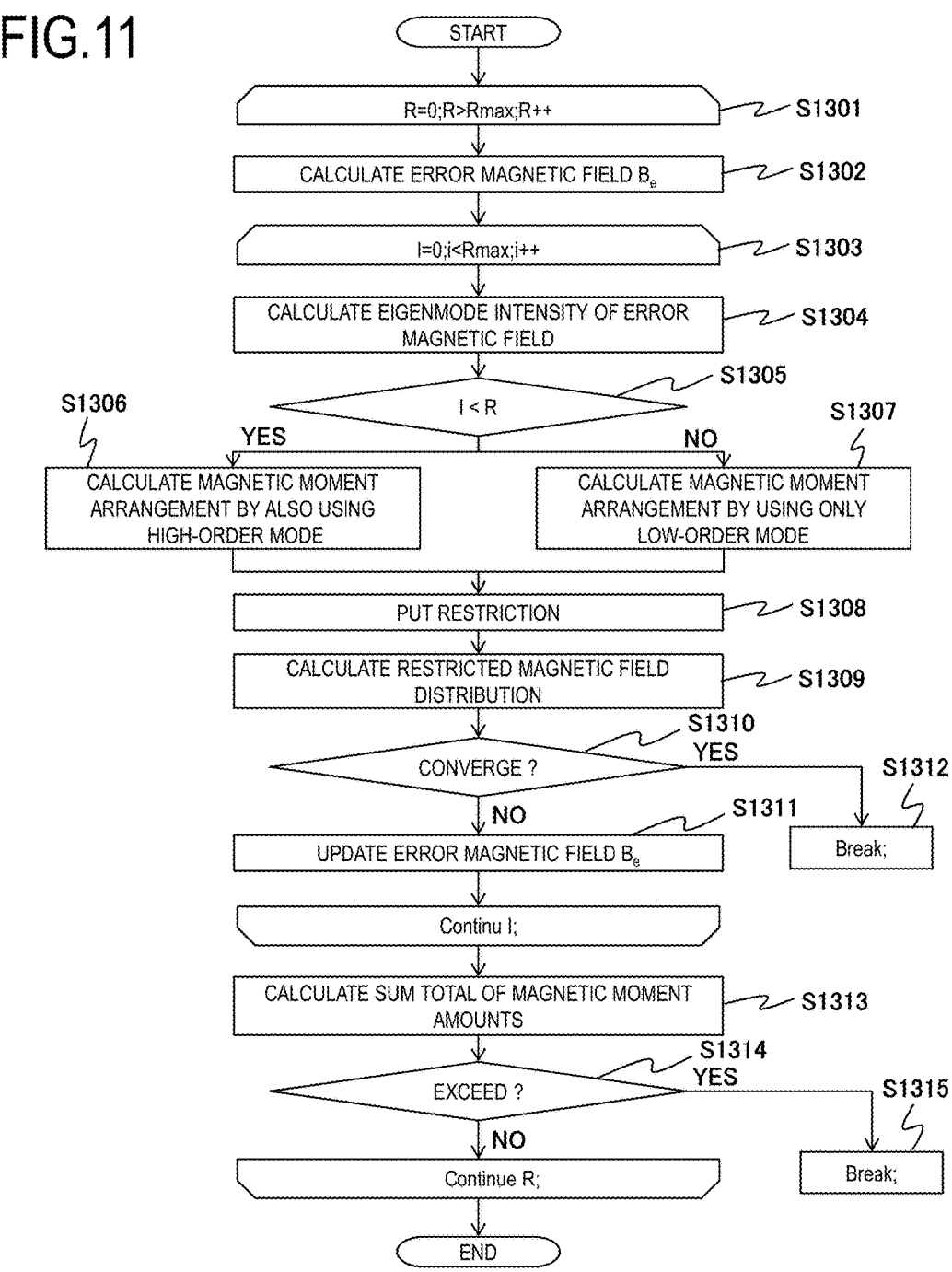
FIG. 11 is a flowchart illustrating a magnetic moment arrangement computation process according to the first embodiment.

A description will be made of a flow of a magnetic moment arrangement computation process performed by the arrangement computation portion 730 of the present embodiment with reference to a process flow of FIG. 11.

As described above, the magnetic moment arrangement computation process of the present embodiment includes a first process loop and a second process loop.

The first process loop is a repetition process in which the number of times of combining eigenmode components divided as a high-order mode with each other is increased until a usable magnetic moment amount is used to the maximum. In other words, the first process loop is a repetition process of increasing a correction amount of a high-order mode. This process loop is repeated until a finish condition is satisfied or the number of times of repetition reaches an upper limit value.

The second process loop is a process based on a restriction condition such as an accommodation amount of each pocket of the container 122 in the magnetic moment arrangement computation process. This process loop is repeated until convergence occurs or the number of times of repetition reaches an upper limit value.

Hereinafter, an upper limit value of the number of times of repetition of both of the process loops is set to Rmax (where Rmax is an integer of 1 or more), a repetition counter (magnetic moment amount adjustment counter) of the first process loop is indicated by R, and a repetition counter (repetition counter) of the second process loop is indicated by i. As the upper limit value Rmax of the number of times of repetition, the number of times for which magnetic moment arrangement computation sufficiently converges is held in advance.

For example, about 500 is set as the upper limit value.

First, the arrangement computation portion 730 initializes the magnetic moment amount adjustment counter (R=0) (step S1301).

The arrangement computation portion 730 computes the error magnetic field $B_e$ which is a correction target in shimming. The error magnetic field $B_e$ is computed according to the following Equation (4) (step S1302).

$$B_e = B_m - B_{Target} \quad (4)$$

Here, $B_{Target}$ is the target intensity of a static magnetic field. $B_e$ and $B_m$ are vectors.

Next, the arrangement computation portion 730 initializes the repetition counter i (i=0) (step S1303).

The arrangement computation portion 730 decomposes the error magnetic field distribution into eigenmode components which are obtained through singular value decomposition. Here, the intensity $C_j$ of each eigenmode of the error magnetic field $B_e$ is calculated (step S1304). Each eigenmode intensity $C_j$ of the error magnetic field $B_e$ can be computed by taking inner product between the error magnetic field $B_e$ and the base $u_j$ of a magnetic field distribution as expressed in the above Equation (3).

The arrangement computation portion 730 compares the repetition counter i with the magnetic moment amount adjustment counter R (step S1305).

As a comparison result, in a case where the repetition counter i is less than the magnetic moment amount adjustment counter R, magnetic moment arrangement $V_k$ is calculated by using the eigenmode intensities $C_j$ with the eigenmode numbers j up to the upper limit value $T_H$ of a high-order mode (step S1306). On the other hand, as a comparison result, in a case where the repetition counter i is equal to or more than the magnetic moment amount adjustment counter R, magnetic moment arrangement $V_k$ is calculated by using the eigenmode intensities $C_j$ with the eigenmode numbers j up to the upper limit value $T_L$ of a low-order mode (step S1307).

Here, the magnetic moment arrangement $V_k$ is computed by using the method disclosed in the above PTL 1. In other words, the magnetic moment amount $V_k$ for arrangement in each pocket k of the container 122 is calculated. Here, k is a number (pocket number) assigned to each pocket.

The magnetic moment arrangement $V_k$ is obtained by multiplying the eigenmode intensity $C_j$ obtained according to Equation (3) by the base $v_j$ of a current potential distribution on the container 122 and by dividing a multiplication result by the singular value $\lambda_j$.

In order to replace the current potential with an amount of iron pieces used for shimming, the current potential may be split in the size m (for example, 1.711 Am$^2$/cc) of the magnetic moment 123 of a saturated iron piece. In other words, the magnetic moment arrangement $V_k$ is obtained according to the following Equation (5).

$$V_k = -\sum_j \left(\frac{v_j C_j}{\lambda_j}\right) / m[cc] \quad (5)$$

Here, $V_k$ calculated according to Equation (5) is written as $V(i,R)_k$ by taking into consideration the repetition counter i and the magnetic moment amount adjustment counter R.

Next, the arrangement computation portion 730 puts restriction based on an accommodation amount of the container 122 (each pocket k thereof) on the calculated magnetic moment amount $V(i,R)_k$ of each pocket k (step S1308).

An amount of magnetic moments which can be stored in the respective pockets k of the container 122 has an upper limit value $V_{max}$ and a lower limit value $V_{min}$. In consideration of this, a magnetic moment amount $V(i,R)_k'$ as a result of the restriction is calculated according to the following Expression (6). Hereinafter, the magnetic moment amount $V(i,R)_k'$ as a result of the restriction will be referred to as a restricted magnetic moment amount.

$$V(i,R)_k' = \begin{cases} V_{max} & \text{if } (V(i,R)_k > V_{max} - V(i-1,R)_k') \\ V_{min} & \text{if } (V(i,R)_k < V_{min} - V(i-1,R)_k') \\ V(i,R)_k + V(i-1,R)_k' & \text{else} \end{cases} \quad (6)$$

Here, $V(i-1,R)_k'$ indicates a restricted magnetic moment amount which is previously calculated in the (i-1)-th process loop, that is, the second process loop. $V(i-1,R)_k'$ is 0 when i is 0.

The arrangement computation portion 730 calculates a magnetic field distribution $B_v$ caused by the magnetic moment 123 disposed in each pocket according to the obtained restricted magnetic moment amount $V(i,R)_k'$ (step S1309). The calculation is performed according to the following Equation (7) by using the response matrix A.

$$B_v = \Sigma_k (A \cdot V(i,R)_k' * m) \quad (7)$$

Here, for the respective pockets k, inner product between the magnetic moment amount $V(i)_k'$ for arrangement in a corresponding pocket and the response matrix A is multiplied by the magnitude m of the magnetic moment of an iron piece, and a sum thereof is computed. The above-described restriction is put on the magnetic field distribution $B_v$, and thus a value thereof is different from a value (i is i−1) obtained one time before the second process loop. Here, $B_v$ is a vector.

The arrangement computation portion 730 calculates a ratio of the magnetic field distribution $B_v$ based on the restricted magnetic moment amount $V(i,R)_k'$ to the original error distribution $B_e$, so as to determine whether or not magnetic moment arrangement computation converges (step S1310). The determination is performed according to the following Expression (8).

$$\frac{\sum B_v}{\sum B_e} < EPS \quad (8)$$

EPS is a threshold value used for a convergence determination reference. For example, a value such as 0.001 (0.1%) may be used. EPS is defined in advance and is stored in a storage device or the like. As mentioned above, the arrangement computation portion 730 determines whether or not the computation of the second process loop based on the repetition counter i of the magnetic moment arrangement computation converges on the basis of whether or not a ratio of the magnetic field distribution $B_v$ to the error distribution $B_e$ is equal to or less than the constant value EPS.

In a case where it is determined that the computation does not converge, first, the arrangement computation portion 730 updates the error magnetic field $B_e$ according to the following Equation (9) (step S1311).

$$B_e = B_e + B_v \quad (9)$$

In addition, i is incremented by 1, and the process of the second process loop is repeatedly performed from step S1304 until the repetition counter i becomes Rmax.

On the other hand, if it is determined that the computation converges in step S1310, the arrangement computation portion 730 finishes the magnetic moment arrangement computation in a case where the number of times of considering a high-order mode is R (step S1312), and computes a sum total $V_{sum}$ of magnetic moment amounts to be used, calculated at that time (step S1313).

The sum total $V_{sum}$ of magnetic moment amounts to be used is a sum of magnetic moment amounts $V(i)_k'$ for arrangement in the respective pockets k, and may be calculated according to the following Equation (10).

$$V_{sum} = \Sigma_k V(i,R) k' \qquad (10)$$

The arrangement computation portion 730 compares the calculated sum total $V_{sum}$ of magnetic moment amounts to be used with the usable iron amount $V_{set}$ which is prepared in advance (step S1314), outputs $V(i,R-1)_k'$ calculated one time before the first process loop as a solution in a case where $V_{sum}$ is more than $V_{set}$ (exceeds) (step S1315), and finishes the process.

On the other hand, in a case where $V_{sum}$ is equal to or less than $V_{set}$, R is incremented by 1, the flow returns to step S1302, and the process of the first process loop is repeatedly performed until the magnetic moment amount adjustment counter R reaches Rmax. Even in a case where R reaches Rmax, $V(i,R-1)_k'$ calculated one time before the first process loop is output as a solution, and finishes the process.

<Examples>

Figure 12:
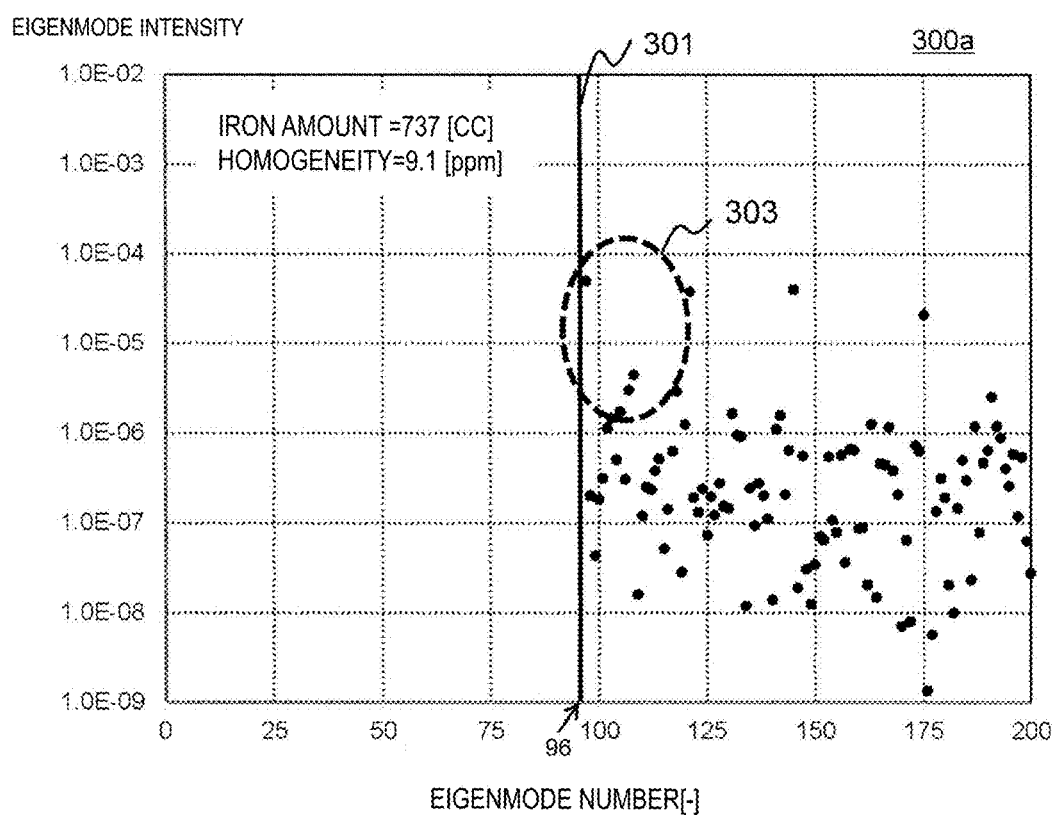
FIG. 12 is a graph of an eigenmode distribution after a shimming process is performed in a method of the related art.
Figure 13:
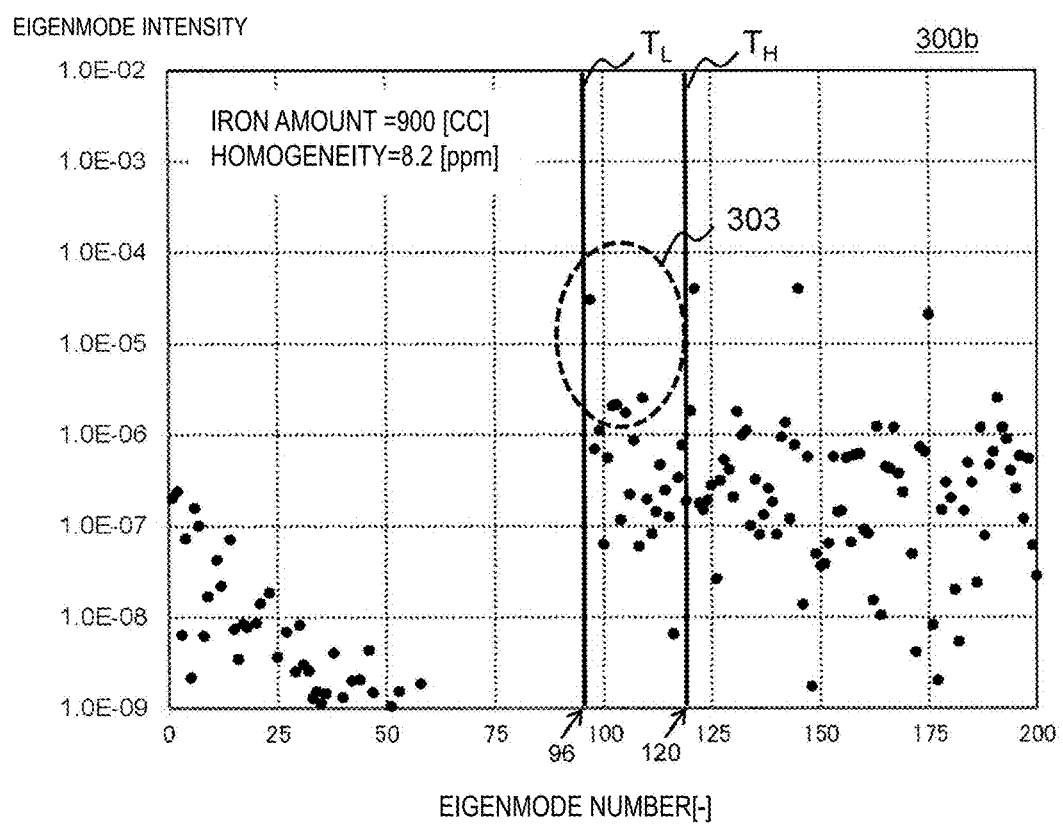
FIG. 13 is a graph of an eigenmode distribution after a shimming process is performed in a method of the first embodiment.

In order to achieve an effect of the present embodiment, FIGS. 12 and 13 illustrate eigenmode distributions 300a and 300b after a shimming process is performed on static magnetic field data indicating the eigenmode distribution 300 in FIG. 4. A usable magnetic moment amount (iron amount) is designated as 900 cc.

FIG. 12 illustrates the eigenmode distribution 300a as a result in a case where sequential correction is performed from a low-order eigenmode in the same manner as in the related art, and FIG. 13 illustrates the eigenmode distribution 300b as a result in a case where correction is performed by applying the present embodiment.

In the method of the related art, the threshold value 301 of the maximum value of the eigenmode number j which is a correction target is set to 96. This is an eigenmode number right before an iron amount considerably increases as illustrated in FIG. 6, and is the same value as the low-order mode upper limit value $T_L$ in a case where a method of the present embodiment which will be described later is applied.

The threshold value 302 of a lower limit value of the intensity of an eigenmode component is set to $10^{-10}$.

The number of main coils of the superconducting magnet at which static magnetic field distribution data is acquired is six. Thus, when the method of the present embodiment is applied, the symmetric base $u_j$ with the identification number #p of 6 (sixth) is used as a threshold value for dividing an eigenmode into a low-order mode and a high-order mode. The eigenmode number j of the sixth symmetric base $u_j$ is 97. Therefore, the upper limit value $T_L$ of a low-order mode is 96. Since an eigenmode number of the seventh symmetric base $u_j$ is 121, the upper limit value $T_H$ of a high-order mode is 120.

In the eigenmode distribution 300a as a result of the method of the related art, as illustrated in FIG. 12, an iron amount used for shimming is 737 cc, and the homogeneity to be expected to reach on a surface of a sphere with 400 mm is 9.1 ppm.

On the other hand, in the eigenmode distribution 300b as a result of the method of the present embodiment, as illustrated in FIG. 13, an iron amount used for shimming is 900 cc which is designated, and a usable iron amount was completely used. The homogeneity to be expected to reach on a surface of a sphere with 400 mm is 8.2 ppm. As mentioned above, as illustrated in FIG. 12, the more favorable homogeneity than in the method of the related art can be obtained.

As can be seen from the eigenmode distributions 300a and 300b, the intensity of an eigenmode is reduced in the eigenmode distribution 300b illustrated in FIG. 13 more than in the eigenmode distribution 300a illustrated in FIG. 12 with respect to a region between $T_L$ and $T_H$ (97 to 120) indicated by a dashed circle 303 in FIGS. 12 and 13.

In a case where the threshold value 301 is set to not 96 but 97 in the method of the related art, a necessary iron amount is 1070 cc, and thus exceeds the usable iron amount of 900 cc as described above.

As described above, the MRI apparatus of the present embodiment measures a magnetic field distribution of a predefined evaluation region in a magnetic field generation device (static magnetic field generation system 120) including a magnetic field adjustment mechanism which adjusts a static magnetic field by using a magnetic moment disposed therein, calculates an error magnetic field distribution which is a difference between the measured magnetic field distribution and a predefined target magnetic field distribution of the evaluation region, decomposes the error magnetic field distribution into components of respective eigenmodes of a magnetic field generated by the magnetic field generation device, obtained through singular value decomposition, and combines correction of a component of a low-order mode with correction of a component of a high-order mode among the eigenmodes so as to calculate arrangement of the magnetic moment for approximately correcting the error magnetic field distribution, in which the low-order mode is an eigenmode group from the first of eigenmode numbers assigned to respective eigenmodes in the magnitude order of singular values to an eigenmode number specified by a first threshold value, in which the high-order mode is an eigenmode group from an eigenmode number one greater than the eigenmode number specified by the first threshold value to an eigenmode number specified by a second threshold value greater than the first threshold value, and in which a correction amount of the component of the high-order mode is smaller than a correction amount of the component of the low-order mode.

A computed magnetic moment amount which is a total magnetic moment amount based on the calculated arrangement of the magnetic moment may be compared with a usable magnetic moment amount which is a usable magnetic moment amount prepared in advance, and the arrangement of the magnetic moment may be repeatedly calculated by increasing a correction amount of the component of the high-order mode until the computed magnetic moment amount exceeds the usable magnetic moment amount.

When the arrangement of the magnetic moment is repeatedly calculated, a correction amount of components of the high-order mode may be increased by increasing the number of times of combining the components of the high-order mode with each other.

The magnetic field generation device may include N (where N is an integer of 1 or more) main coils, among the respective eigenmodes, an identification number may be assigned to an eigenmode in which a base of the eigenmode is axisymmetric with respect to a direction of a magnetic field generated by the magnetic field generation device and is plane-symmetric with respect to a plane which is orthogonal to the magnetic field direction in the magnitude order of singular values, and an eigenmode number which is one smaller than an eigenmode number of an N-th eigenmode from a small identification number is set as the first threshold value, and, among the respective eigenmodes, an eigenmode number which is one smaller than an eigenmode number of a (N+1)-th eigenmode from a small identification number may be set as the second threshold value.

As mentioned above, according to the present embodiment, in shimming for correcting an error magnetic field, with respect to each eigenmode having undergone singular value decomposition, a low-order mode which has the great influence is reliably corrected, and a high-order mode which has the small influence is corrected as long as a magnetic moment amount can be used. Thus, as a magnetic moment amount to be used is increased, the accuracy of correction is also improved.

Therefore, according to the present embodiment, it is possible to make it compatible that a high-order eigenmode component is also corrected as much as possible, and a given magnetic moment amount is effectively used as much as possible. In other words, according to the present embodiment, it is possible to effectively use a usable magnetic moment amount and to realize highly accurate shimming.

Second Embodiment

Next, a second embodiment of the present invention will be described. In the first embodiment, in the repetition process of computing magnetic moment arrangement, a magnetic moment (iron amount) which is prepared in advance is completely used by changing the number of times for which an eigenmode divided as a high-order mode is included in computation. On the other hand, in the present embodiment, eigenmodes other than a low-order mode are all divided as high-order modes, a correction amount is adjusted by adjusting the intensity of the eigenmodes divided as the high-order mode, and a magnetic moment (iron amount) which is prepared in advance is used as completely as possible.

An MRI apparatus of the present embodiment fundamentally has the same configuration as that of the MRI apparatus 100 of the first embodiment. However, there is a difference in a correction amount adjustment method, and thus a process in the shimming unit 700 of the control system 170 differs. Hereinafter, the present embodiment will be described focusing on a configuration which is different from that in the first embodiment.

The shimming unit 700 of the present embodiment also performs magnetic moment arrangement computation until the magnetic moment amount $V_{set}$ which is prepared in advance is used to the maximum while increasing a correction amount of a high-order eigenmode. In this case, a correction amount is adjusted by adjusting the eigenmode intensity. Thus, the shimming unit 700 of the present embodiment includes a magnetic field measurement portion 710, a low-order/high-order determination portion 720, and an arrangement computation portion 730 in the same manner as in the first embodiment.

A process in the magnetic field measurement portion 710 is the same as that in the first embodiment. However, processes in the low-order/high-order determination portion 720 and the arrangement computation portion 730 are different from those in the first embodiment.

The low-order/high-order determination portion 720 of the present embodiment determines only the upper limit value $T_L$ of a low-order region. As described above, in the present embodiment, eigenmodes other than a low-order mode are all divided as high-order modes. In other words, in the present embodiment, the second threshold value $T_H$ is the maximum value of the eigenmode number j.

The arrangement computation portion 730 of the present embodiment changes a correction amount of the eigenmode intensity $C_j$ of a high-order mode in a case where a calculated usable magnetic moment amount $V_{sum}$ is smaller than a prepared magnetic moment amount $V_{seT}$ whenever magnetic moment arrangement is determined while putting on restriction according to the method of the related art, and repeatedly performs the process until the maximum value $V_{sum}$ is used as much as possible.

The correction amount is changed by changing a coefficient which is multiplied by the eigenmode intensity $C_j$ of a high-order region. The multiplied coefficient will be referred to as an eigenmode intensity coefficient.

In other words, the arrangement computation portion 730 of the present embodiment multiplies an eigenmode component by a predefined intensity coefficient when repeatedly performing calculation of magnetic moment arrangement, and the intensity coefficient is determined so that a correction amount of the high-order mode component is increased according to an increase of the number of times of repetition.

The intensity coefficient is expressed by the eigenmode number j, and a function of a counter (magnetic moment amount adjustment counter) R indicating the number of repetition processes, repeatedly performed, of increasing a correction amount of a high-order mode, and is expressed by, for example, the following Expression (11).

$$SC_j(R) = \begin{cases} 0 & \text{if } (j < T_L) \\ 1 - \dfrac{1}{(R+1)*\text{EXP}(j-T_L)} & \text{else} \end{cases} \quad (11)$$

Here, $SC_j(R)$ is an eigenmode intensity coefficient which is a function of the eigenmode number j used for R-th repetition.

Figure 14:
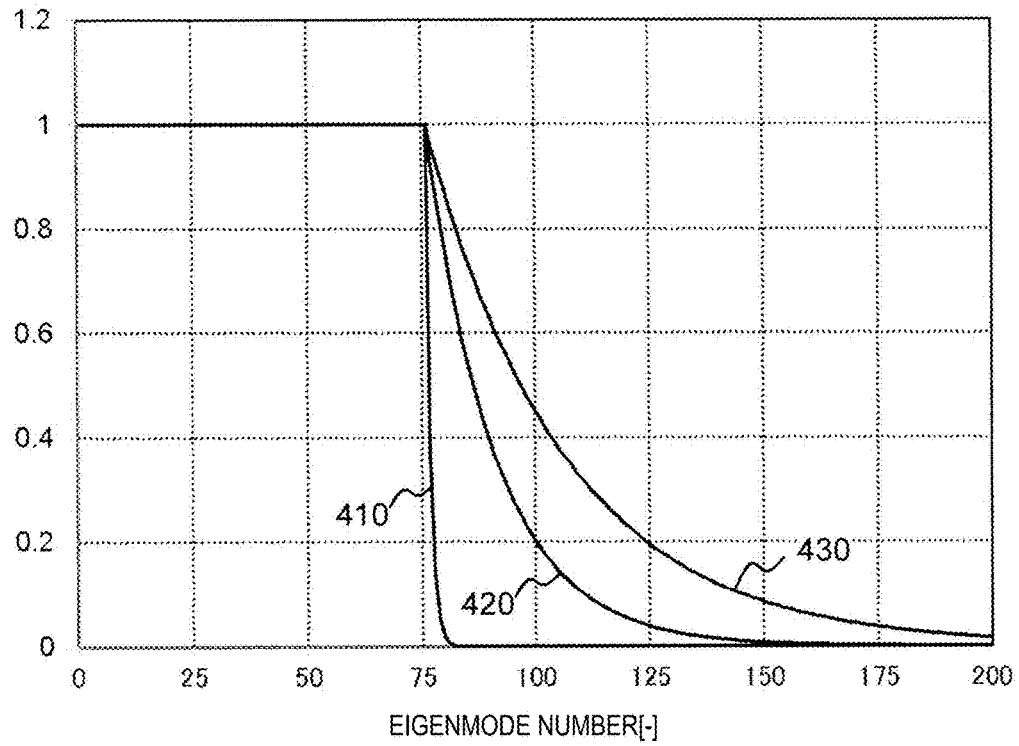
FIG. 14 is a graph of an intensity coefficient according to a second embodiment.

FIG. 14 illustrates an example of an intensity coefficient determined according to the above Expression (11). In FIG. 14, a graph 410 is an example of a graph of the intensity coefficient $SC_j(R)$ in a case where R is 0, a graph 420 is an example of a graph of the intensity coefficient $SC_j(R)$ in a case where R is 15, and a graph 430 is an example of a graph of the intensity coefficient $S_j(R)$ in a case where R is 30.

In any graph, a value of the coefficient comes close to 0 as the eigenmode number j increases, that is, an eigenmode becomes high order. Consequently, a correction amount is reduced as an eigenmode becomes high order.

A formula describing an intensity coefficient is not limited to the above Expression (11) using an exponential function. Other functions may be used as long as the functions are not intended to completely make a high-order component zero.

The intensity coefficient $SC_j(R)$ corresponding to the eigenmode number j and the number of times of repetition R is prepared in advance, and is held in the storage device 172 or the like.

[Flow of Process]

A flow of the entire shimming process of the present embodiment is the same manner as the process in the first embodiment.

[Low-Order/High-Order Determination Process]

Figure 15:
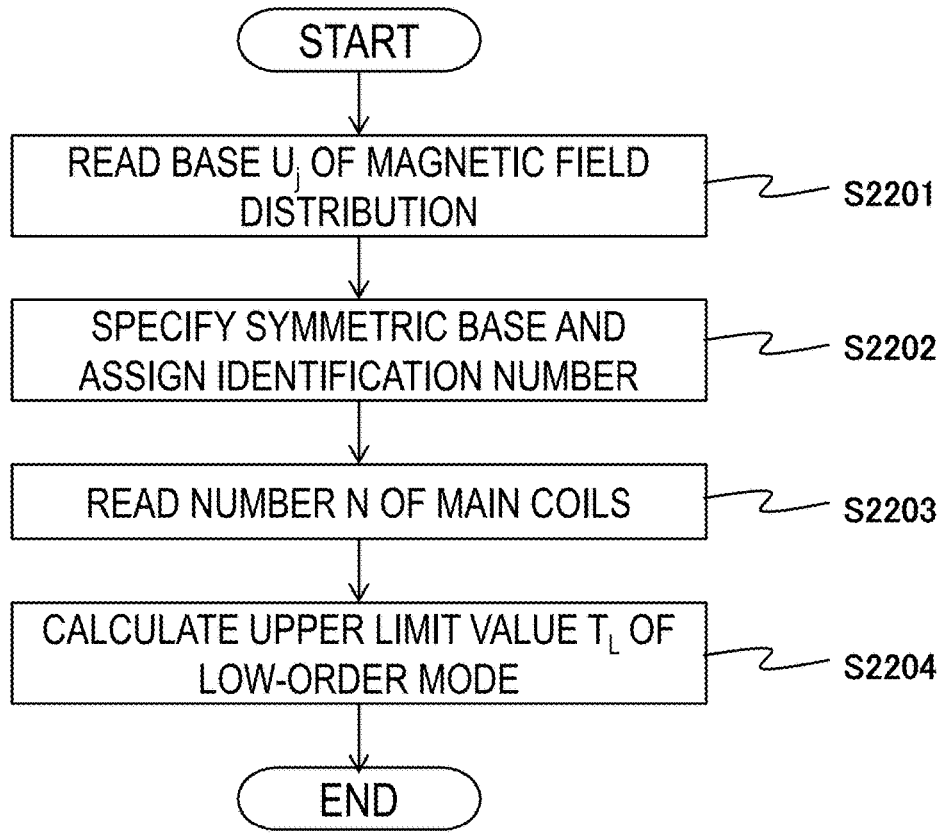
FIG. 15 is a flowchart illustrating a low-order/high-order determination process according to the second embodiment.

A description will be made of a flow of a low-order/high-order determination process performed by the low-order/high-order determination portion 720 of the present embodiment with reference to FIG. 15.

First, the low-order/high-order determination portion 720 reads the bases $u_j$ of a magnetic field distribution obtained through singular value decomposition of the response matrix A (step S2201). The symmetric base $u_j$ is extracted from the read bases $u_j$ (step S2202). The identification number #p is assigned to the symmetric base $u_j$ in the order (the magnitude order of singular values) of the eigenmode number j of a corresponding eigenmode as described above.

The low-order/high-order determination portion 720 reads the number N of main coils 125 (step S2203). The number of main coils is held in advance as apparatus information or the like.

Next, the low-order/high-order determination portion 720 calculates the upper limit value $T_L$ of a low-order mode according to the above-described method by using the subscript j of the base with the identification number #p of N in the symmetric base $u_j$ (step S2204). The process is finished.

[Arrangement Computation Process]

Figure 16:
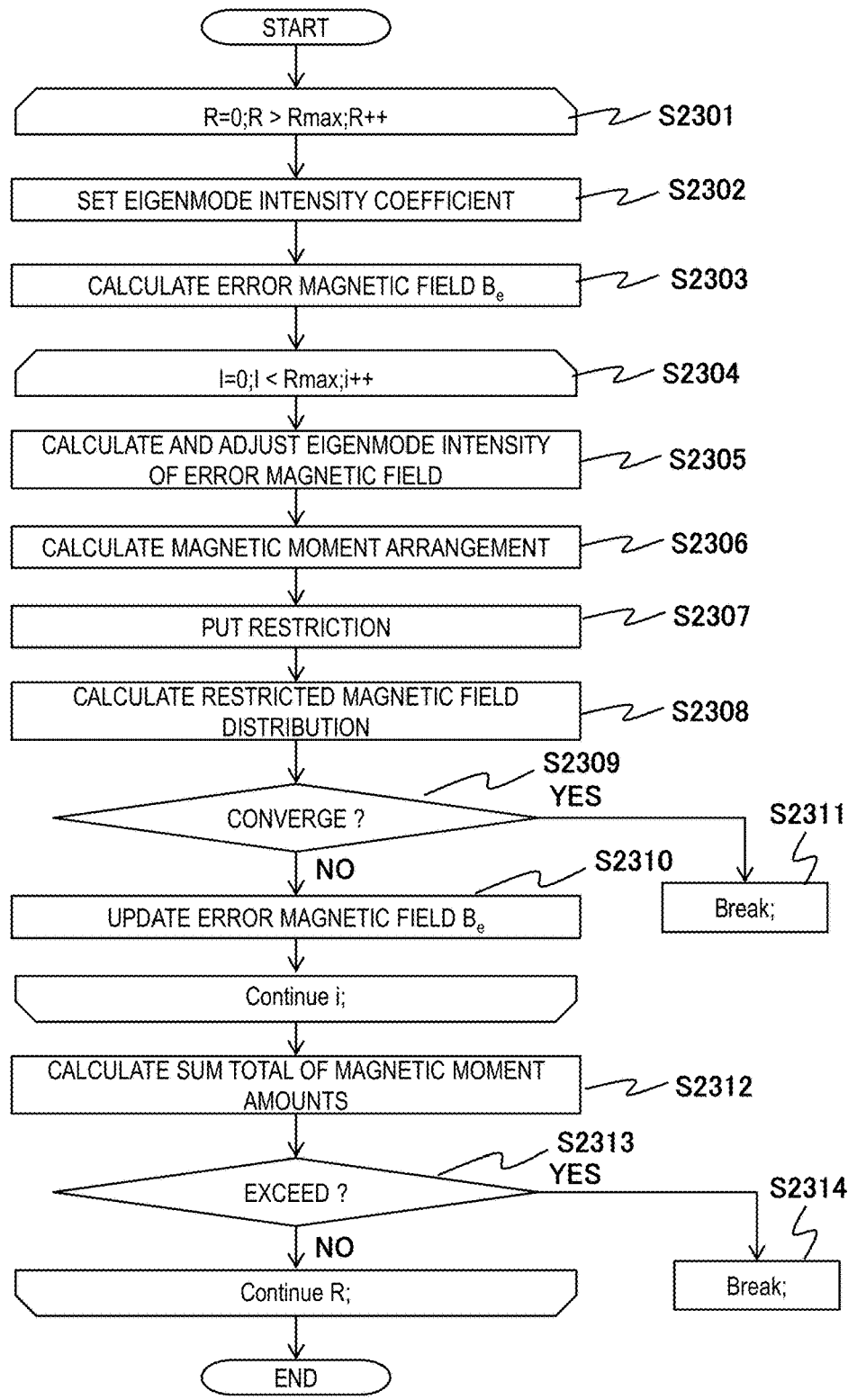
FIG. 16 is a flowchart illustrating a magnetic moment arrangement computation process according to the second embodiment.

Next, a description will be made of a flow of a magnetic moment arrangement determination process performed by the arrangement computation portion 730 of the present embodiment with reference to a process flow of FIG. 16.

Also in the present embodiment, a magnetic moment arrangement determination process includes a first process loop of increasing a correction amount of a high-order mode, and a second process loop based on a restriction condition such as an accommodation amount of each pocket of the container 122. Also in the present embodiment, in the same manner as in the first embodiment, an upper limit value of the number of times of repetition of both of the process loops is set to Rmax (where Rmax is an integer of 1 or more), a repetition counter (magnetic moment amount adjustment counter) of the first process loop is indicated by R, and a repetition counter (repetition counter) of the second process loop is indicated by i. As the upper limit value Rmax of the number of times of repetition, the number of times for which magnetic moment arrangement computation sufficiently converges is held in advance. For example, about 500 is set as the upper limit value.

First, the arrangement computation portion 730 initializes the magnetic moment amount adjustment counter (R=0) (step S2301).

Next, the arrangement computation portion 730 sets a predefined eigenmode intensity coefficient $SC_j(R)$ according to the magnetic moment amount adjustment counter R (step S2302).

The arrangement computation portion 730 computes the error magnetic field $B_e$ which is a correction target in shimming (step S2303). The error magnetic field $B_e$ is computed according to the following Equation (4) in the same manner as in the first embodiment.

Next, the arrangement computation portion 730 initializes the repetition counter i (i=0) (step S2304).

The arrangement computation portion 730 calculates the intensity $C_j$ of each eigenmode of the error magnetic field $B_e$ according to the same method as that in the first embodiment (step S2305). At this time, the arrangement computation portion 730 of the present embodiment adjusts the eigenmode intensity C3 according to the following Equation (12) by using the eigenmode intensity coefficient $SC_j(R)$ and the threshold value $T_L$.

$$C_j = (B_e \cdot u_j) * SC_j(R) \qquad (12)$$

Next, the arrangement computation portion 730 calculates the magnetic moment amount $V(i,R)_k$ of each pocket without setting a threshold value based on the eigenmode number j (step S2306). Computation of magnetic moment arrangement is performed according to the same method as that in the first embodiment.

The arrangement computation portion 730 puts restriction based on the container 122 on the calculation result $V(i,R)_k$ according to the following Expression (6) in the same manner as in the first embodiment, and thus calculates a restricted magnetic moment amount $V(i,R)_k'$ (step S2307).

The arrangement computation portion 730 calculates a magnetic field distribution $B_y$ caused by the magnetic moment 123 disposed in each pocket by using the calculated restricted magnetic moment amount $V(i,R)_k'$ according to the above Equation (7) in the same manner as in the first embodiment (step S2308), and determines whether or not the magnetic field distribution $B_y$ converges according to the above Expression (8) (step S2309).

In a case where it is determined that convergence does not occur, first, the arrangement computation portion 730 updates the error magnetic field $B_e$ according to the above Equation (9) in the same manner as in the first embodiment (step S2310), increments i by 1, and repeatedly performs the process of the second process loop from step S2304 until the repetition counter i becomes Rmax.

On the other hand, if it is determined that convergence occurs, the arrangement computation portion 730 finishes the magnetic moment arrangement computation in the same manner as in the first embodiment (step S2311), computes a sum total $V_{sum}$ of magnetic moment amounts to be used, calculated at that time according to the above Equation (10), and compares the sum total $V_{sum}$ with the usable iron amount $V_{set}$ which is prepared in advance (step S2312).

In a case where $V_{sum}$ is larger than (exceeds) $V_{set}$, $V(i,R-1)_k'$ calculated one time before is output as a solution (step S2314), and finishes the process. On the other hand, in a case where $V_{sum}$ is equal to or less than $V_{set}$, R is incremented by 1, the flow returns to step S2302, and the process of the first process loop is repeatedly performed until the magnetic moment amount adjustment counter R reaches Rmax. Also in the present embodiment, even in a case where R reaches Rmax, $V(i,R-1)_k'$ calculated one time before the first process loop is output as a solution, and finishes the process.

As described above, the MRI apparatus of the present embodiment measures a magnetic field distribution of a predefined evaluation region in a magnetic field generation device (static magnetic field generation system 120) including a magnetic field adjustment mechanism which adjusts a static magnetic field by using a magnetic moment disposed therein, calculates an error magnetic field distribution which is a difference between the measured magnetic field distribution and a predefined target magnetic field distribution of the evaluation region, decomposes the error magnetic field distribution into components of respective eigenmodes of a magnetic field generated by the magnetic field generation device, obtained through singular value decomposition, and combines correction of a component of a low-order mode with correction of a component of a high-order mode among the eigenmodes so as to calculate arrangement of the magnetic moment for approximately correcting the error magnetic field distribution, in which the low-order mode is an eigenmode group from the first of eigenmode numbers assigned to respective eigenmodes in the magnitude order of singular values to an eigenmode number specified by a first threshold value, in which the high-order mode is an eigenmode group from an eigenmode number one greater than the eigenmode number specified by the first threshold value to an eigenmode number specified by a second threshold value greater than the first threshold value, and in which a correction amount of the component of the high-order mode is smaller than a correction amount of the component of the low-order mode.

A computed magnetic moment amount which is a total magnetic moment amount based on the calculated arrangement of the magnetic moment may be compared with a usable magnetic moment amount which is a usable magnetic moment amount prepared in advance, and the arrangement of the magnetic moment may be repeatedly calculated by increasing a correction amount of the component of the high-order mode until the computed magnetic moment amount exceeds the usable magnetic moment amount.

When the arrangement of the magnetic moment is repeatedly calculated, a predefined intensity coefficient may be multiplied by the component of the eigenmode, and the intensity coefficient may be determined so that a correction amount of components of the high-order mode is increased according to an increase of the number of times of repetition.

As mentioned above, according to the present embodiment, in the same manner as in the first embodiment, since a low-order mode which has the great influence is reliably corrected, and a high-order mode which has the small influence is corrected as long as a magnetic moment amount can be used, it is possible to effectively use a usable magnetic moment amount and to realize highly accurate shimming.

According to the present embodiment, it is possible to designate a reduction ratio and a distribution thereof in the intensity of each high-order eigenmode. In other words, it is possible to reduce a high-order eigenmode component in a shape of a function intended by a worker performing shimming.

The present invention is not limited to the above-described embodiments. An eigenmode number of a symmetric base correlated with the number of main coils is used to differentiate a high order and a low order from each other, but an eigenmode number may be designated at random or may be designated with an iron amount required for correction as a reference.

In the second process loop, determination is performed with a ratio of a sum total value of the magnetic field distribution $B_v$ to a sum total value of the error magnetic field $B_e$ as a reference by using the above Expression (8), but is not limited thereto. For example, a ratio of a sum (a sum total value of the updated error magnetic field $B_e$) of the magnetic field distribution $B_v$ and the error magnetic field $B_e$ to a sum total value of the error magnetic field $B_e$ may be used as a reference.

A description has been made of the method in which a usable magnetic moment amount is designated, and magnetic moment arrangement which is possible within restriction thereof is obtained, but a high-order mode may be included in computation only any number of times without designating a magnetic moment amount, or magnetic moment arrangement may be obtained by using any intensity coefficient.

The method of the first embodiment and the method of the second embodiment may be combined with each other.

In the above-described respective embodiments, each function of the control system 170 is realized by the CPU 171 loading a program stored in the storage device 172 to a memory, and executing the program. Some or all of the functions of the control system 170 may be realized by hardware such as an application specific integrated circuit (ASIC) or a field-programmable gate array (FPGA). Various pieces of data used for processing each function, and various pieces of data generated during processing are stored in the storage device 172.

In the above-described respective embodiments, the shimming unit 700 has been described to be realized by the control system 170 of the MRI apparatus 100, but is not limited thereto. The shimming unit 700 may be realized as, for example, a magnetic field adjustment device on an information processing device which can perform transmission and reception of data with the MRI apparatus 100 and is independent from the MRI apparatus 100. A magnetic field adjustment target apparatus may not be an MRI apparatus.

REFERENCE SIGNS LIST

100 MRI APPARATUS, 101 OBJECT, 120 STATIC MAGNETIC FIELD GENERATION SYSTEM, 121 SUPERCONDUCTING MAGNET, 122 CONTAINER, 123 MAGNETIC MOMENT, 124 EVALUATION SPACE (EVALUATION REGION), 125 MAIN COIL, 130 GRADIENT MAGNETIC FIELD GENERATION SYSTEM, 131 GRADIENT MAGNETIC FIELD COIL, 132 GRADIENT MAGNETIC FIELD POWER SOURCE, 140 SEQUENCER, 150 SIGNAL TRANSMISSION SYSTEM, 151 SIGNAL TRANSMISSION COIL, 152 SIGNAL TRANSMISSION PROCESSING UNIT, 160 SIGNAL RECEPTION SYSTEM, 161 SIGNAL RECEPTION COIL, 162 SIGNAL RECEPTION PROCESSING UNIT, 170 CONTROL SYSTEM, 171 CPU, 172 STORAGE DEVICE, 173 DISPLAY DEVICE, 174 INPUT DEVICE, 180 SENSOR, 300 EIGENMODE DISTRIBUTION, 300a EIGENMODE DISTRIBUTION, 300b EIGENMODE DISTRIBUTION, 301 THRESHOLD VALUE, 302 THRESHOLD VALUE, 303 REGION, 310 GRAPH OF CHANGE IN IRON AMOUNT, 311 GRAPH OF CHANGE IN HOMOGENEITY, 312 GRAPH OF CHANGE IN IRON AMOUNT, 320 GRAPH OF CHANGE IN HOMOGENEITY, 410 INTENSITY COEFFICIENT, 420 INTENSITY COEFFICIENT, 430 INTENSITY COEFFICIENT, 700 SHIMMING UNIT, 710 MAGNETIC FIELD MEASUREMENT PORTION, 720 LOW-ORDER/HIGH-ORDER DETERMINATION PORTION, 730 ARRANGEMENT COMPUTATION PORTION

The invention claimed is:

1. A magnetic moment arrangement calculation method for magnetic field adjustment comprising:
    measuring a magnetic field distribution of a predefined evaluation region in a magnetic field generation device including a magnetic field adjustment mechanism which adjusts a static magnetic field by using a magnetic moment disposed therein;
    calculating an error magnetic field distribution which is a difference between the measured magnetic field distribution and a predefined target magnetic field intensity of the evaluation region;
    decomposing the error magnetic field distribution into components of respective eigenmodes of a magnetic field generated by the magnetic field generation device, obtained through singular value decomposition; and
    combining correction of a component of a low-order mode with correction of a component of a high-order mode among the eigenmodes so as to calculate arrangement of the magnetic moment for approximately correcting the error magnetic field distribution,
    wherein the low-order mode is an eigenmode group from the first of eigenmode numbers assigned to respective eigenmodes in the magnitude order of singular values to an eigenmode number specified by a first threshold value, wherein the high-order mode is an eigenmode group with an eigenmode number more than the first threshold value, and wherein a correction amount of the component of the high-order mode is smaller than a correction amount of the component of the low-order mode.

2. The magnetic moment arrangement calculation method for magnetic field adjustment according to claim 1, wherein a computed magnetic moment amount which is a total magnetic moment amount based on the calculated arrangement of the magnetic moment is compared with a usable magnetic moment amount which is a usable magnetic moment amount prepared in advance, and the arrangement of the magnetic moment is repeatedly calculated by increasing a correction amount of the component of the high-order mode until the computed magnetic moment amount exceeds the usable magnetic moment amount.

3. The magnetic moment arrangement calculation method for magnetic field adjustment according to claim 1, wherein the magnetic field generation device includes N (where N is an integer of 1 or more) main coils, and wherein the first threshold value is defined according to the number N of main coils of the magnetic field generation device.

4. The magnetic moment arrangement calculation method for magnetic field adjustment according to claim 3, wherein, among the respective eigenmodes, an identification number is assigned to an eigenmode in which a base of the eigenmode is axisymmetric with respect to a direction of a magnetic field generated by the magnetic field generation device and is plane-symmetric with respect to a plane which is orthogonal to the magnetic field direction in the magnitude order of singular values, and an eigenmode number which is one smaller than an eigenmode number of an N-th eigenmode from a small identification number is set as the first threshold value.

5. The magnetic moment arrangement calculation method for magnetic field adjustment according to claim 2, wherein, when the arrangement of the magnetic moment is repeatedly calculated, a correction amount of components of the high-order mode is increased by increasing the number of times of combining the components of the high-order mode with each other.

6. The magnetic moment arrangement calculation method for magnetic field adjustment according to claim 2, wherein the high-order mode is an eigenmode group from an eigenmode number one greater than the eigenmode number specified by the first threshold value to an eigenmode number specified by a second threshold value greater than the first threshold value.

7. The magnetic moment arrangement calculation method for magnetic field adjustment according to claim 6, wherein the second threshold value is the maximum value of the eigenmode number, wherein, when the arrangement of the magnetic moment is repeatedly calculated, a predefined intensity coefficient is multiplied by the component of the eigenmode, and wherein the intensity coefficient is determined so that a correction amount of components of the high-order mode is increased according to an increase of the number of times of repetition.

8. The magnetic moment arrangement calculation method for magnetic field adjustment according to claim 7, wherein the magnetic field generation device includes N (where N is an integer of 1 or more) main coils, wherein, among the respective eigenmodes, an identification number is assigned to an eigenmode in which a base of the eigenmode is axisymmetric with respect to a direction of a magnetic field generated by the magnetic field generation device and is plane-symmetric with respect to a plane which is orthogonal to the magnetic field direction in the magnitude order of singular values, and an eigenmode number which is one smaller than an eigenmode number of an N-th eigenmode from a small identification number is set as the first threshold value, and wherein, among the respective eigenmodes, an eigenmode number which is one smaller than an eigenmode number of a (N+1)-th eigenmode from a small identification number is set as the second threshold value.

9. The magnetic moment arrangement calculation method for magnetic field adjustment according to claim 1, wherein, when the arrangement of the magnetic moment is calculated, an accommodation amount of the magnetic moment of the magnetic field adjustment mechanism is searched for as a restriction condition.

10. A magnetic field adjustment device comprising:

a magnetic field distribution measurement portion that measures a magnetic field distribution of a predefined evaluation region in a magnetic field generation device including a magnetic field adjustment mechanism which adjusts a static magnetic field by using a magnetic moment disposed therein;

an arrangement computation portion that computes arrangement of the magnetic moment for correcting an error magnetic field distribution which is a difference between the measured magnetic field distribution and a predefined target magnetic field intensity of the evaluation region; and a low-order/high-order determination portion that divides each eigenmode of a magnetic field generated by the magnetic field generation device into a low-order mode which is an eigenmode group from the first of eigenmode numbers assigned to respective eigenmodes in the magnitude order of singular values to an eigenmode number specified by a first threshold value, and a high-order mode which is an eigenmode group with an eigenmode number more than the first threshold value, wherein the arrangement computation portion decomposes the error magnetic field distribution into components of respective eigenmodes obtained through singular value decomposition, and combines correction of a component of the low-order mode with correction of a component of the high-order mode so as to calculate the arrangement of the magnetic moment for approximately correcting the error magnetic field distribution, and wherein a correction amount of the component of the high-order mode is smaller than a correction amount of the component of the low-order mode.

11. The magnetic field adjustment device according to claim 10, wherein the magnetic field generation device is a static magnetic field generation system of a magnetic resonance imaging apparatus.

12. The magnetic field adjustment device according to claim 10, wherein the high-order mode is an eigenmode group from an eigenmode number one greater than the eigenmode number specified by the first threshold value to an eigenmode number specified by a second threshold value greater than the first threshold value.

13. A non-transitory computer readable medium storing a program, which when executed by a computer, causing the computer to function as:
- a magnetic field distribution measurement portion that measures a magnetic field distribution of a predefined evaluation region in a magnetic field generation device including a magnetic field adjustment mechanism which adjusts a static magnetic field by using a magnetic moment disposed therein;
- an arrangement computation portion that computes arrangement of the magnetic moment for correcting an error magnetic field distribution which is a difference between the measured magnetic field distribution and a predefined target magnetic field intensity of the evaluation region; and
- a low-order/high-order determination portion that divides each eigenmode of a magnetic field generated by the magnetic field generation device into a low-order mode which is an eigenmode group from the first of eigenmode numbers assigned to respective eigenmodes in the magnitude order of singular values to an eigenmode number specified by a first threshold value, and a high-order mode which is an eigenmode group with an eigenmode number more than the first threshold value, wherein the arrangement computation portion decomposes the error magnetic field distribution into components of respective eigenmodes obtained through singular value decomposition, and combines correction of a component of the low-order mode with correction of a component of the high-order mode so as to calculate the arrangement of the magnetic moment for approximately correcting the error magnetic field distribution, and wherein a correction amount of the component of the high-order mode is smaller than a correction amount of the component of the low-order mode.

14. The non-transitory computer readable medium according to claim 13, wherein the high-order mode is an eigenmode group from an eigenmode number one greater than the eigenmode number specified by the first threshold value to an eigenmode number specified by a second threshold value greater than the first threshold value.

* * * * *